(12) United States Patent
Doctor et al.

(10) Patent No.: US 7,754,461 B2
(45) Date of Patent: Jul. 13, 2010

(54) LARGE-SCALE PRODUCTION OF HUMAN SERUM BUTYRYLCHOLINESTERASE AS A BIOSCAVENGER

(75) Inventors: Bhupendra P. Doctor, Potomac, MD (US); Ashima Saxena, Fairfax, VA (US); Wei Sun, Gaithersburg, MD (US); Chunyuan Luo, North Potomac, MD (US); Prasanthi Tipparaju, Rockville, MD (US); Irwin Koplovitz, Bel Air, MD (US); David E. Lenz, Belcamp, MD (US); Michelle C. Ross, Edgewood, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/733,246

(22) Filed: Apr. 10, 2007

(65) Prior Publication Data

US 2007/0184045 A1 Aug. 9, 2007

Related U.S. Application Data

(63) Continuation of application No. 11/244,173, filed on Oct. 6, 2005, now abandoned.

(60) Provisional application No. 60/618,064, filed on Oct. 9, 2004.

(51) Int. Cl.
*C12N 9/16* (2006.01)
*C12N 9/14* (2006.01)
*C12N 9/00* (2006.01)
*A61K 38/46* (2006.01)

(52) U.S. Cl. ............... 435/196; 435/183; 435/195; 424/94.6

(58) Field of Classification Search ............... 435/196, 435/195, 183; 424/94.6
See application file for complete search history.

(56) References Cited

U.S. PATENT DOCUMENTS 5,272,080 A * 12/1993 Lynch .................... 435/197
5,944,648 A * 8/1999 Cornay .................... 494/33
2003/0148488 A1* 8/2003 Ralston et al. ............ 435/196

OTHER PUBLICATIONS

Yamada. 1972. Studies on a method for separating aspartate- and alanine-aminotransferase in fowl blood plasma. Japanese Journal of Veterinary Science, (1972) vol. 34, No. 4, pp. 207-221.*
Purification and characterization of lysozyme 2002, http://www.usm.maine.edu/~rhodes/BiochemLab/Text/HdtPurLys/HDTPurLys03.html.*
Principles of Continuous Flow Centrifugation. 2004 Beckman Couter Technical Information.*
Ashani Y. (2000) Prospective of Human butyrylcholinesterase as a detoxifying antidote and potential regulator of controlled-release drugs. Drug Development Research 50:298-308.*
Raveh et al. Human butyrylcholinesterase as a general prophylactic antidote for nerve agent toxicity. In vitro and in vivo quantitative characterization. Biochem Pharmacol. Jun. 22, 1993;45(12):2465-74.*
Ralston et al. Use of procainamide gels in the purification of human and horse serum cholinesterases. Biochem J. Apr. 1, 1983;211(1):243-50.*
Nerve gas autoinjector administration, web published in Dec. 1, 2001; http://www.emsa.cahwnet.gov/para/auto%20injector.pdf.*
Grunwald et al. (1997) Large-scale purification and long-term stability of human butyrylcholinesterase: a potential bioscavanger drug. J. Biochem. Biophys. Methods 34:123-135.*

* cited by examiner

*Primary Examiner*—Taeyoon Kim
(74) *Attorney, Agent, or Firm*—Elizabeth Arwine

(57) ABSTRACT

Disclosed herein are methods for the large-scale preparation of human butyrylcholinesterase (HuBChE) preparations from Cohn Fraction IV-4. As disclosed, the methods provide HuBChE preparations that are about 99% or more pure with recovery yields of about 60%. Also disclosed are the pharmacokinetics, safety and toxicity, stability and efficacy of the HuBChE preparations.

15 Claims, 5 Drawing Sheets

LARGE-SCALE PRODUCTION OF HUMAN SERUM BUTYRYLCHOLINESTERASE AS A BIOSCAVENGER

CROSS REFERENCE TO RELATED APPLICATIONS

This application is a continuation of U.S. patent application Ser. No. 11/244,173, filed 6 Oct. 2005, abandoned, which claims the benefit of U.S. Provisional Patent Application No. 60/618,064, filed 9 Oct. 2004, which are herein incorporated by reference in their entirety.

ACKNOWLEDGMENT OF GOVERNMENT SUPPORT

Employees of the United States Army made this invention. The government has rights in the invention.

BACKGROUND OF THE INVENTION

1. Field of the Invention

The present invention generally relates to a method for the large-scale production of human serum butyrylcholinesterase (HuBChE) from Cohn Fraction IV-4 paste.

2. Description of the Related Art

Exposure to organophosphorus compounds (OPs) in the form of nerve agents and pesticides poses an ever increasing threat to military and civilian populations. The serious medical challenges posed by chemical warfare agents to both the military and civilian health care systems became evident in the Iran-Iraq conflict and the 1995 Tokyo subway incident, respectively. The acute toxicity of OPs is usually attributed to their irreversible inhibition of acetylcholinesterase (AChE). The resultant increase in acetylcholine concentration manifests at the cholinergic synapses of both the peripheral and central nervous systems, which precipitates a cholinergic crisis characterized by miosis, increased tracheobronchial and salivary secretions, bronchoconstriction, bradycardia, fasciculations, behavioral incapacitation, muscular weakness, and convulsions, ultimately culminating in death by respiratory failure. Current antidotal regiments for OP poisoning consist of a combination of pretreatment with a spontaneously reactivating AChE inhibitor such as pyridostigmine bromide, and post-exposure therapy with anticholinergic drugs such as atropine sulfate and oximes such as 2-PAM chloride. See Gray (1984) Drug Metab. Rev. 15:557-589. Although these antidotal regimens are effective in preventing lethality of animals from OP poisoning, they do not prevent postexposure incapacitation, convulsions, performance deficits or in many cases, permanent brain damage. See Dirnhuber et al. (1979) J. Pharm. Pharmacol. 31:295-299; McLeod (1985) Fundam. Appl. Toxicol. 5:S10-S16; and Dunn & Sidell (1989) J. Am. Med. Assoc. 262:649-652. These problems stimulated the development of enzyme bioscavengers as a pretreatment to sequester highly toxic OPs before they reach their physiological targets and prevent the in vivo toxicity of OPs and post exposure incapacitation.

Among the enzymes examined as potent scavengers of highly toxic OP nerve agents, significant advances have been made using ChEs. Exogenous administration of plasma-derived ChEs such as AChE from fetal bovine serum (FBS) and BChE from human and equine serum (Eq), in both rodent and non-human primate models, has been successfully used as a safe and efficacious prophylactic treatment to prevent poisoning by OP compounds. See Doctor et al. (2001) "New approaches to Medical protection against chemical warfare nerve agents" CHEMICAL WARFARE AGENTS: TOXICITY AT LOW LEVELS, NYC, CRC Press, pp. 191-214. In contrast to the currently used multi-drug treatment, ChEs as prophylactic agents have the advantage of being single pretreatment scavengers capable of protecting against multiple $LD_{50}$'s of a wide variety of potent OPs without the requirement of additional post-exposure therapy.

Of the ChEs evaluated so far, HuBChE has several advantages as an exogenously administered prophylactic for human use. See Ashani (2000) Drug Dev. Res. 50:298-308. First, it reacts rapidly with all highly toxic OPs, offering a broad range of protection for nerve agents including, soman, sarin, tabun, and VX. Studies in mice, rats, guinea pigs and rhesus monkeys clearly demonstrated that HuBChE could function as an antidote for all OP nerve agents. See Raveh et al. (1993) Biochem. Pharmacol. 45:2465-2474; Brandeis et al. (1993) Pharmacol. Biochem. Behav. 46:889-896; Allon et al. (1998) Toxicol. Sci. 43:121-128; and Raveh et al. (1997) Toxicol. Pharmacol. 145:43-53. These studies also showed that pretreatment with HuBChE was effective in preventing mortality as well as development of behavioral deficits without the need for additional post-exposure therapy. Second it possesses a very long retention time in human circulation and is readily absorbed from sites of injection. Although the reported values of half-life of exogenously administered HuBChE in humans vary from 3.4 to 11 days, they suggest that the circulatory stability of the enzyme is sufficient for its use as a pretreatment drug. See Ostergaard et al. (1988) Acta Anaesthesiologica Scandinavica 32:266-269. The extended stability of exogenously administered HuBChE was also demonstrated in mice and rats, guinea pigs, and rhesus monkeys. These results suggest that a single injection of HuBChE will provide long-lasting protection if used as a prophylactic treatment. Third, since the enzyme is from a human source, it should not produce any adverse immunological responses upon repeated administration into humans. The lack of reports indicating untoward side-effects in humans following plasma transfusions and i.v. injections of partially purified HuBChE support our contention. See Cascio et al. (1988) Minerva Anestesiol. 54:337-338. Similarly, the exogenous administration of 13-20 mg/kg doses of HuBChE did not seem to affect gross behavior in mice, rats or guinea pigs and no behavior alterations were reported in rhesus monkeys treated with 13-34 mg of HuBChE.

Extrapolation of data obtained from prophylaxis experiments with HuBChE in four species suggests that a dose of 200 mg of HuBChE as a prophylactic treatment can protect humans from exposure of up to 2 $LD_{50}$ of soman. Smaller doses of 50 mg of enzyme would be sufficient to provide protection against low-level exposure to nerve agents. In addition to its use as a pretreatment for a variety of wartime scenarios, including covert actions, it also has potential use for first responders (civilians) reacting to intentional/accidental nerve gas release or pesticide overexposure. In addition, since HuBChE catalyzes the hydrolysis of cocaine and short-acting muscle relaxants succinylcholine and mivacurium, it could be an effective treatment for cocaine intoxication, as well as succinylcholine- and mivacurium-induced apnea.

The foremost requirement to advance HuBChE as a bioscavenger for human use was to obtain sufficient amounts of purified enzyme for conducting animal and clinical studies. Although a procedure for the purification of HuBChE from human plasma, which contains about 2 mg of enzyme per liter of plasma, was described, this source is not suitable for producing large quantities of HuBChE for clinical and commercial uses.

Thus a need exists for methods for the large-scale production of HuBChE.

SUMMARY OF THE INVENTION

The present invention generally relates to the large-scale production of HuBChE preparations.

In some embodiments the present invention provides a method for obtaining an amount of a human butyrylcholinesterase preparation which comprises subjecting about 2 or more kilograms, preferably about 10 to 500 kilograms, more preferably about 100 to 500 kilograms, most preferably about 300 to 500 kilograms, of Cohn Fraction IV-4 paste to affinity chromatography followed by anion exchange chromatography. In some embodiments, the amount of Cohn Fraction IV-4 is about 80 kilograms or more, preferably about 80 kilograms. In some embodiments, the method comprises diluting the Cohn Fraction IV-4 paste by about ten-fold with water to obtain a suspension and then adjusting the suspension to a pH of about 4.5 to about 5.5, preferably about 4.7 to about 5.2, more preferably about 4.8 to about 5.0, most preferably about 4.9. In some embodiments, the method comprises centrifuging the suspension using a continuous flow centrifuge at about 7400 to about 7900 rpm, preferably about 7500 to about 7800 rpm, more preferably about 7600 to about 7700 rpm, most preferably about 7663 rpm at a flow rate of about 2 to about 6 kilograms per minute, preferably about 3 to about 5 kilograms per minute, more preferably about 4 kilograms per minute to obtain a supernatant. In some embodiments, the method comprises adjusting the supernatant to a pH of about 7.0 to about 9.0, preferably about 7.5 to about 8.5, more preferably about 8.0. In some embodiments, the method comprises filtering the supernatant with a 0.65 µm filter cartridge. In some embodiments, the affinity chromatography and the anion exchange chromatography are performed once. In some embodiments, the affinity chromatography is conducted using a procainamide column. In some embodiments, the anion exchange chromatography is conducted using a DEAE sepharose fast flow column. In some embodiments, the amount of the human butyrylcholinesterase preparation obtained is about 60% w/w of that present in Cohn Fraction IV-4 paste. In some embodiments, the human butyrylcholinesterase preparation is about 99% or more pure. In some embodiments, the human butyrylcholinesterase preparation in lyophilized form is storage stable at about –20° C. to about 45° C. and is also stable in circulation upon storage at about –20° C. for at least two years. In some embodiments, the butyrylcholinesterase in the human butyrylcholinesterase preparation exhibits a mean retention time of more than about 70 hours and an elimination half-life of more than about 35 hours in macaques. In some embodiments, the human butyrylcholinesterase preparation is non-toxic. Specifically, in some embodiments, the human butyrylcholinesterase preparation is physiological, histopathological, or behavioral non-toxic to a subject when administered thereto.

In some embodiments, the present invention provides a human butyrylcholinesterase preparation made by subjecting about 2 or more kilograms, preferably about 10 to 500 kilograms, more preferably about 100 to 500 kilograms, most preferably about 300 to 500 kilograms, of Cohn Fraction IV-4 paste to affinity chromatography followed by anion exchange chromatography. In some embodiments, the amount of Cohn Fraction IV-4 is about 80 kilograms or more, preferably about 80 kilograms. In some embodiments, the method comprises diluting the Cohn Fraction IV-4 paste by about ten-fold with water to obtain a suspension and then adjusting the suspension to a pH of about 4.5 to about 5.5, preferably about 4.7 to about 5.2, more preferably about 4.8 to about 5.0, most preferably about 4.9. In some embodiments, the method comprises centrifuging the suspension using a continuous flow centrifuge at about 7400 to about 7900 rpm, preferably about 7500 to about 7800 rpm, more preferably about 7600 to about 7700 rpm, most preferably about 7663 rpm at a flow rate of about 2 to about 6 kilograms per minute, preferably about 3 to about 5 kilograms per minute, more preferably about 4 kilograms per minute to obtain a supernatant. In some embodiments, the method comprises adjusting the supernatant to a pH of about 7.0 to about 9.0, preferably about 7.5 to about 8.5, more preferably about 8.0. In some embodiments, the method comprises filtering the supernatant with a 0.65 µm filter cartridge. In some embodiments, the affinity chromatography and the anion exchange chromatography are performed once. In some embodiments, the affinity chromatography is conducted using a procainamide column. In some embodiments, the anion exchange chromatography is conducted using a DEAE sepharose fast flow column. In some embodiments, the amount of the human butyrylcholinesterase preparation obtained is about 60% w/w of that present in Cohn Fraction IV-4 paste. In some embodiments, the human butyrylcholinesterase preparation is about 99% or more pure. In some embodiments, the human butyrylcholinesterase preparation in lyophilized form is storage stable at about –20° C. to about 45° C. and is also stable in circulation upon storage at about –20° C. for at least two years. In some embodiments, the butyrylcholinesterase in the human butyrylcholinesterase preparation exhibits a mean retention time of more than about 70 hours and an elimination half-life of more than about 35 hours in macaques. In some embodiments, the human butyrylcholinesterase preparation is non-toxic. Specifically, in some embodiments, the human butyrylcholinesterase preparation is physiological, histopathological, or behavioral non-toxic to a subject when administered thereto. In some embodiments, the human butyrylcholinesterase preparation is packaged as a single dose in an autoinjector. In some embodiments, the present invention provides a pharmaceutical preparation comprising the human butyrylcholinesterase preparation described herein and a pharmaceutically acceptable carrier.

In some embodiments, the present invention provides a method of treating, preventing, or inhibiting toxicity to an organophosphorus compound in a subject which comprises administering to the subject the human butyrylcholinesterase preparation made by subjecting about 2 or more kilograms, preferably about 10 to 500 kilograms, more preferably about 100 to 500 kilograms, most preferably about 300 to 500 kilograms, of Cohn Fraction IV-4 paste to affinity chromatography followed by anion exchange chromatography. In some embodiments, the amount of Cohn Fraction IV-4 is about 80 kilograms or more, preferably about 80 kilograms. In some embodiments, the method comprises diluting the Cohn Fraction IV-4 paste by about ten-fold with water to obtain a suspension and then adjusting the suspension to a pH of about 4.5 to about 5.5, preferably about 4.7 to about 5.2, more preferably about 4.8 to about 5.0, most preferably about 4.9. In some embodiments, the method comprises centrifuging the suspension using a continuous flow centrifuge at about 7400 to about 7900 rpm, preferably about 7500 to about 7800 rpm, more preferably about 7600 to about 7700 rpm, most preferably about 7663 rpm at a flow rate of about 2 to about 6 kilograms per minute, preferably about 3 to about 5 kilograms per minute, more preferably about 4 kilograms per minute to obtain a supernatant. In some embodiments, the method comprises adjusting the supernatant to a pH of about 7.0 to about 9.0, preferably about 7.5 to about 8.5, more preferably about 8.0. In some embodiments, the method comprises filtering the supernatant with a 0.65 μm filter cartridge. In some embodiments, the affinity chromatography and the anion exchange chromatography are performed once. In some embodiments, the affinity chromatography is conducted using a procainamide column. In some embodiments, the anion exchange chromatography is conducted using a DEAE sepharose fast flow column. In some embodiments, the amount of the human butyrylcholinesterase preparation obtained is about 60% w/w of that present in Cohn Fraction IV-4 paste. In some embodiments, the human butyrylcholinesterase preparation is about 99% or more pure. In some embodiments, the human butyrylcholinesterase preparation in lyophilized form is storage stable at about −20° C. to about 45° C. and is also stable in circulation upon storage at about −20° C. for at least two years. In some embodiments, the butyrylcholinesterase in the human butyrylcholinesterase preparation exhibits a mean retention time of more than about 70 hours and an elimination half-life of more than about 35 hours in macaques. In some embodiments, the human butyrylcholinesterase preparation is non-toxic. Specifically, in some embodiments, the human butyrylcholinesterase preparation is physiologically, histopathologically, or behaviorally non-toxic to a subject when administered thereto. In some embodiments, the human butyrylcholinesterase preparation is packaged as a single dose in an autoinjector. In some embodiments, the present invention provides a method of treating, preventing, or inhibiting toxicity to an organophosphorus compound in a subject which comprises administering to the subject a pharmaceutical preparation according to the present invention.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein.

DETAILED DESCRIPTION OF THE INVENTION

As provided herein, a combination of resuspension of Cohn Fraction IV-4 paste, its pH adjustment, centrifugation, and filtration, followed by procainamide affinity and DEAE fast-flow ion-exchange chromatography was developed to purify tens of grams of HuBChE.

Cohn Fraction IV-4 paste, a by-product of human plasma generated during the production of human proteins, such as γ-globulin, was identified as a rich source of HuBChE. This paste contains about 150 mg of enzyme per kg, which is much higher than human plasma and contains much lesser quantities of other plasma proteins due to the fractionation steps deployed in the production process. Usually Cohn Fraction IV-4 is regarded as a waste product of the fractionated plasma and is disposed of after addition of large quantities of Celite®. This results in the inactivation of most of the enzyme activity reducing its activity to about 3 mg/kg, thereby rendering this paste unsuitable for the isolation of HuBChE. Therefore, the most suitable source of HuBChE is freshly prepared Cohn Fraction IV-4 paste prior to the addition of Celite®, a filter aid.

About 8 g of purified enzyme was obtained from 80 kg of Cohn Fraction IV-4 paste using this procedure. The thermal stability of this enzyme was determined in lyophilized and liquid form. The enzyme activity was stable when stored in liquid form at 4° C. and 25° C. and in lyophilized form at 4° C., 25° C., 37° C. or 45° C. for at least 2 years. The enzyme did not exhibit any toxicity in mice or guinea pigs even at doses up to 30 and 60 mg/kg, respectively, as measured by general observation, serum chemistry, complete blood count, and gross and histological tissues changes.

In contrast to the currently used multi-drug treatment, HuBChE as prophylactic agent has the advantage of being a single pretreatment scavenger capable of protecting against multiple $LD_{50}$'s of a wide variety of potent OPs without the requirement of additional post-exposure therapy. HuBChE will be the first successful pretreatment/treatment that can afford protection against not only mortality, but also against the adverse physiological and behavioral effects of nerve agent exposure. This technology will provide sustained maximum protection to the war fighter under the most adverse battlefield conditions without performance degradation or interruption of the pace of operations.

Thus in one preferred embodiment, the invention pertains to a process as herein described, wherein the Cohn Fraction IV-4 paste is fresh.

In another preferred embodiment, the invention pertains to a process as herein described, wherein the Cohn Fraction IV-4 paste has not been subjected to an addition of Celite®.

In another preferred embodiment, the invention pertains to a process as herein described, wherein said resuspending comprises resuspending the Cohn Fraction IV-4 paste in water. In an especially preferred embodiment, the water is CWFI.

Alternatively, the Cohn Fraction IV-4 paste can be resuspended in other pharmaceutically acceptable solvents.

In another preferred embodiment, the invention pertains to a process as herein described, wherein said adjusting comprises adjusting the pH of the solution to a pH about pH 8.0, prior to subjecting the solution to procainamide affinity chromatography. In an especially preferred embodiment, the solution is adjusted to about pH 8.0 by treating the solution with a sodium hydroxide solution.

In another preferred embodiment, the invention pertains to a process as herein described, wherein said subjecting the solution to procainamide affinity chromatography comprises eluting the HuBChE from a chromatography column packed with procainamide sepharose gel using sodium chloride solution.

In another preferred embodiment, the invention pertains to a process as herein described, wherein said subjecting the solution to DEAE ion-exchange chromatography comprises eluting the HuBChE from a chromatography column packed with DEAE sepharose fast flow gel.

Figure 1A:
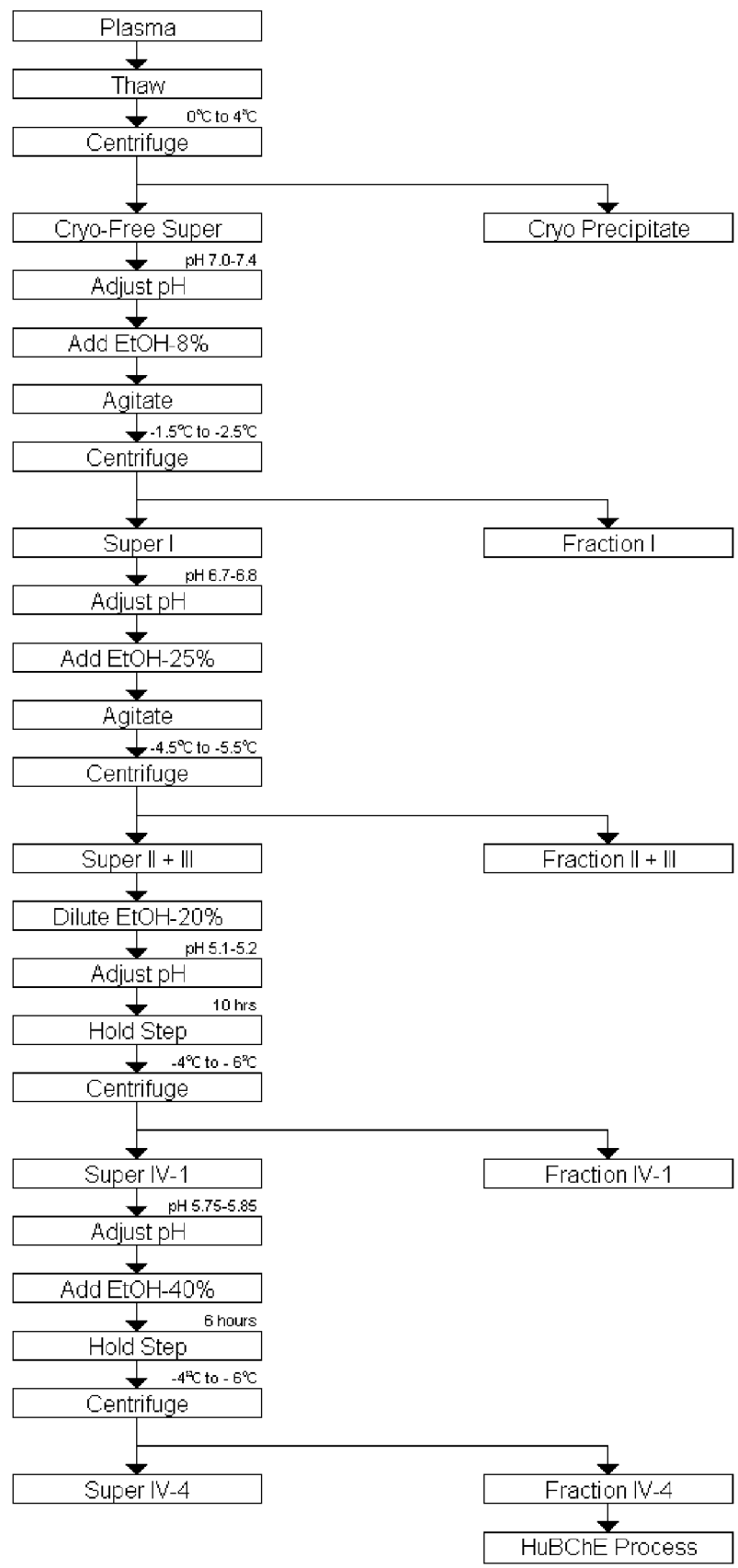
FIG. 1A is a schematic describing a method for obtaining Cohn Fraction IV-4.
Figure 1B:
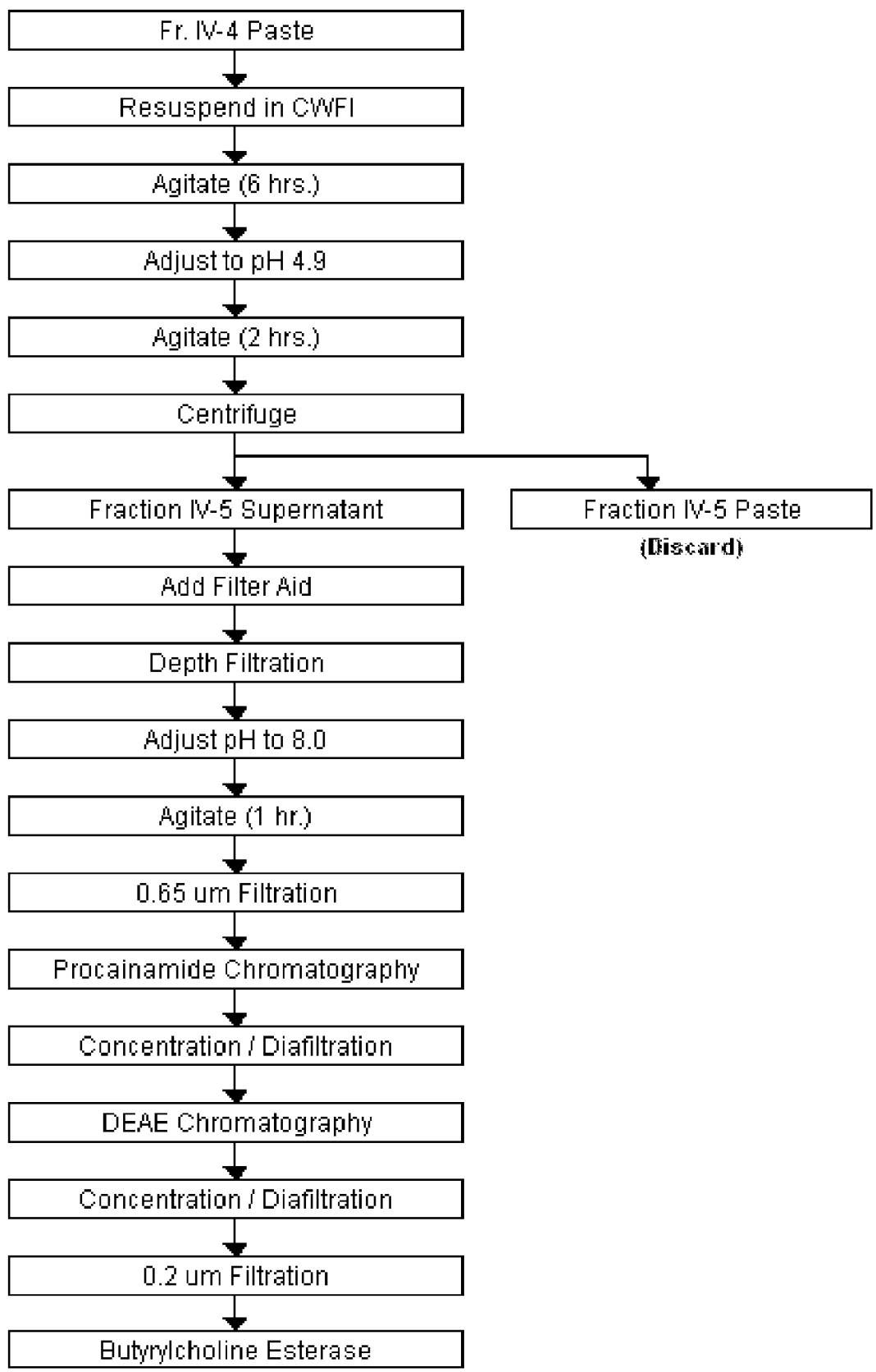
FIG. 1B is a schematic describing the method according to the present invention for obtaining HuBChE from Cohn Fraction IV-4.

An overview of the procedure that can be used to practice the present invention starting with plasma is shown in FIG. 1A and FIG. 1B. Alternatively, Cohn Fraction IV-4 paste can be obtained frozen. However, as noted above, it is preferred that the Cohn Fraction IV-4 paste is fresh.

Stepwise Production of HuBChE from Cohn Fraction IV-4 Paste

Step 1: A total of 80 kg of Cohn Fraction IV-4 paste (Medimmune Inc., MD) was resuspended in 720 L of Cold Water for Injection (CWFI). The resuspension was mixed for 6 to 8 hours at 0° C. to 4° C. The pH of the resuspension was adjusted to 4.90 (from 5.73) by the addition of 1.91 kg of 80× concentrated sodium acetate (NaAc) buffer. The Fraction IV-4 resuspension was centrifuged in the Carr P 18 Powerfuge at 7,500 rpm at a feed flow rate of 4.0 kg/min. Temperature was maintained at 2° C. to 8° C. This resulted in 712 L of supernatant and 16.8 kg of paste.

Step 2: Three Cuno® 60LA filter cartridges were installed in a Cuno® filter housing and flushed with 100 L of water. A total of 0.75 kg of acid washed Celite® 521 was added to about 498 L of CWFI and mixed for 30 minutes. This mixture was then transferred through the Cuno® filters to precoat the filter surface. This was followed by a 200 L rinse with 20 mM NaAc buffer, pH 4.9. A total of 2.85 kg of acid washed Celite® 521 was added to the 712 L of product and mixed for about 1 hour (4 g filter aid/kg of product). The product was then filtered through the Cuno® filters. Following filtration the housing was chased with buffer to recover additional product. The final filtered volume (including buffer chase) was about 963 L.

Step 3: The product was adjusted to pH 8.04 by the addition of 50.34 L of 0.4 N NaOH solution. This resulted in 1016 L of product. The product was then filtered through a 30 inch 0.65 µm filter cartridge. Final quantity after filtration was about 1005 L.

Figure 2:
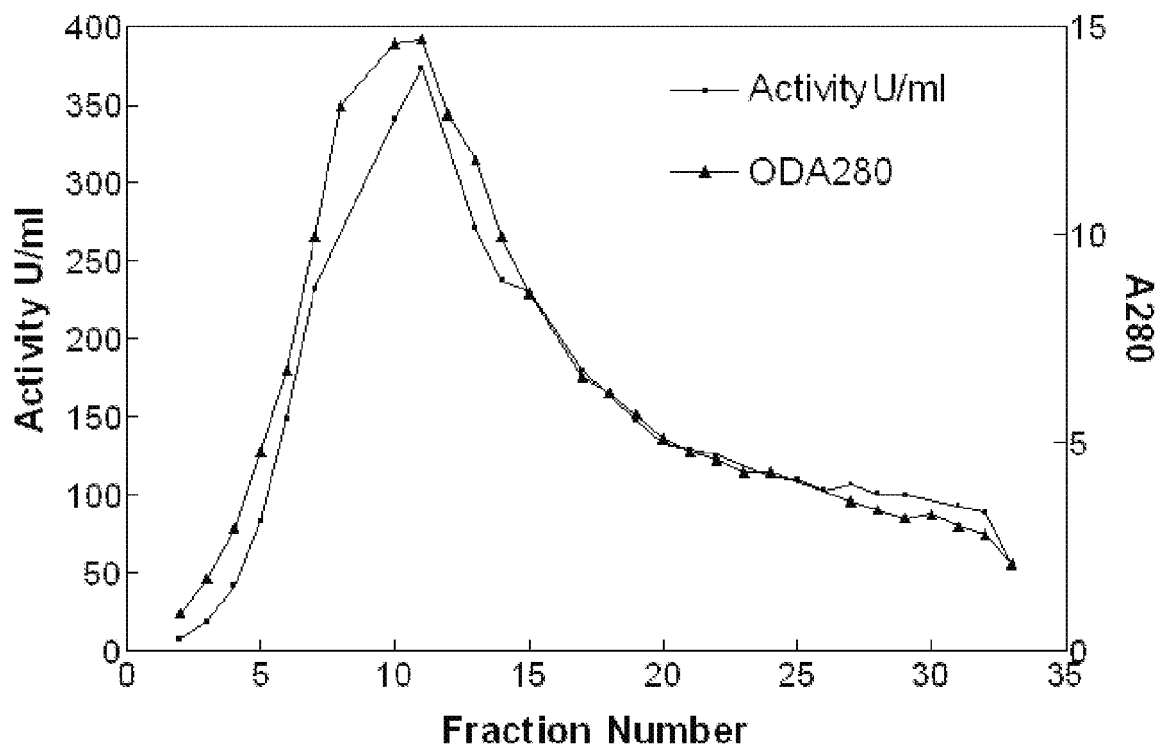
FIG. 2 is a graph depicting the elution of HuBChE from a procainamide affinity column Run #1. The activity and $A_{280}$ of each fraction are shown. The volume of each fraction (#4-32) was 800 ml and #33-35 was 20 L. On the basis of activity and $A_{280}$, fractions 4 to 35 were pooled. The pool (87 L) contained 8.4 million units of BChE activity.

Step 4: Procainamide sepharose gel was packed into an Amicon® P630 X 500 column to a bed height of 8.5 cm (CV=25 L). The procainamide sepharose column was equilibrated with a minimum of 5 column volumes of equilibration buffer (25 mM sodium phosphate pH 8.0 and 1 mM EDTA). Product was loaded onto the column at about 1100 ml/min with a total loading time of about 16 hours. The column was washed with 134 L equilibration buffer at 1100 ml/min. The column was then washed with 1440 L equilibration buffer+ 0.075 M NaCl at about 155 ml/min. Elution was performed with equilibration buffer+1.0 M NaCl at a flow rate of 800 ml/min. Fractions were monitored for BChE activity and $A_{280}$ and pooled. The pool was 80 to 90 L representing about 8 million units of activity as shown in FIG. 2.

Step 5: A Millipore® Pellicon apparatus, with 1.0 m² of Millipore® 100 kDa membrane, was washed with WFI and equilibration buffer prior to use. The procainamide pool was concentrated to 9.8 L and then diafiltered with more than 16× volumes of equilibration buffer. The final diafiltered volume was about 12 L.

Step 6: DEAE sepharose fast flow gel was packed into a Millipore® VA250 X 500 column to a bed height of 38 cm (CV=18.6 L). The DEAE column was equilibrated with a minimum of 5 column volumes of equilibration buffer. Diafiltered product was then loaded onto the column at a flow rate of 75 ml/min. Following loading, the column was washed with 58 L of equilibration buffer at 75 ml/min. The column was then washed with equilibration buffer+0.05 M NaCl at 75 ml/min for about 40 column volumes. The column was eluted with a 10 column volume gradient from equilibration buffer+ 0.05 M NaCl (low) to equilibration buffer+0.3 M NaCl (high) at a flow rate of 75 ml/min. Fractions of 500 ml were collected manually starting at the first appearance of protein as detected by a flow through UV monitor $A_{280}$. A total of about 25 L of product was pooled for further processing.

Figure 3:
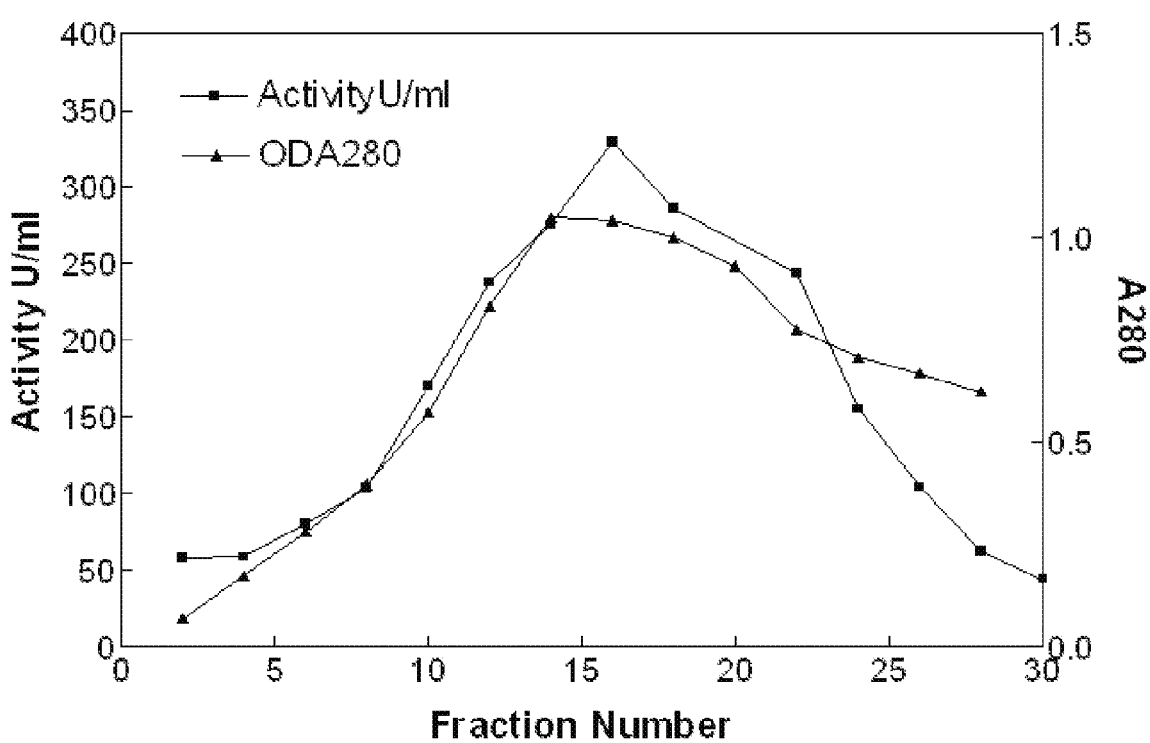
FIG. 3 is a graph depicting the elution of HuBChE from a DEAE fast flow column Run #1. The activity and $A_{280}$ of each fraction are shown. The volume of each fraction was 500 ml. On the basis of activity and $A_{280}$, fractions 3 to 26 were pooled. The pool contained 5.5 million units of BChE activity.

Step 7: A Millipore® Pellicon apparatus, assembled with 1.0 m² of Millipore® 100 kD membrane, was washed with WFI and equilibration buffer prior to use. The DEAE pool was concentrated to 5 L and then diafiltered with equilibration buffer. The final volume of the concentrated diafiltered product was about 8 L and about 5 million units corresponding to about 8 g of HuBChE as shown in FIG. 3.

Step 8: A Millipore® Pellicon apparatus, assembled with 2.5 m² of Millipore® 30 kD membrane, was washed with WFI and equilibration buffer prior to use. The DEAE pool from step 7 was concentrated further to obtain about 850 ml and about 5 million units corresponding to about 7.4 g of HuBChE. The enzyme was filter sterilized using a 0.22 µm filter and 3 ml of solution containing 25 mg of HuBChE was aliquoted into 10 ml glass vials, lyophilized and stored at −20° C.

Assay of HuBChE Activity

BChE activity was determined spectrophotometrically at 25° C. according to the Ellman method. See Ellman et al. (1961) Biochem. Pharmacol. 7:88-95, which is herein incorporated by reference. The assay mixture contained 1 mM butyrylthiocholine as the substrate and 1 mM 5,5-dithiobis-nitrobenzoic acid in 50 mM sodium phosphate, pH 8.0. One unit of the enzyme activity is defined as the amount required to hydrolyze 1 µmol of substrate/min.

Assay of HuBChE Protein

BChE protein was assayed by monitoring the absorbance at 280 nm. An extinction coefficient of 1.92 for a solution containing 1 mg/ml of HuBChE was used for calculating the specific activity of these preparations. Table 1 below shows the recovery of HuBChE activity and protein from Cohn Fraction IV-4 paste.

TABLE 1

Recovery of HuBChE Activity and Protein from Cohn Fraction IV-4 Paste

| Step | Units (×1000) | Total protein (g) |
|---|---|---|
| Resuspension | 9512 | 22500 |
| pH Adjustment to 4.9 | 9794 | 23780 |
| Centrifugation | 8295 | 19860 |

TABLE 1-continued

Recovery of HuBChE Activity and Protein from Cohn Fraction IV-4 Paste

| Step | Units (×1000) | Total protein (g) |
|---|---|---|
| Filter Aid Addition | 5985 | 13160 |
| Depth Filtration | 9341 | 15890 |
| pH Adjustment to 8.0 | 8433 | 16660 |
| 0.65 μm Filtration | 8744 | 17290 |
| Procainamide Column | 8478 | 62.2 |
| DEAE Column | 5517 | 8.6 |
| Concentration 1 | 5461 | 8.6 |
| Concentration 2 | 5112 | 7.4 |

Viral Elimination Step

A dedicated viral elimination step may be included in this purification scheme after step 5 as follows: Calculate the amount of TNBP required to treat the product (0.003 ml/g). Calculate the amount of 20% Triton X-100 required to treat the product (0.0526 ml/g). Combine the TNBP and 20% triton X-100 and mix for 15 minutes. Slowly add the TNBP/Triton mixture to the product. Once all the solvent detergent has been added, mix for 15 minutes. Transfer the treated product to a clean container and hold for a minimum of 4 hours. Assay sample for total protein and BChE activity and load on the DEAE fast flow column.

Sodium Dodecyl Sulfate Polyacrylamide Gel Electrophoresis

Electrophoresis was performed on a 10% polyacrylamide gel according to the procedure of Laemmli known in the art. The reduced form was obtained by boiling enzyme samples with 5% mercaptoethanol for 5 minutes. Each lane was loaded with about 10 to about 20 μl sample containing about 5 to about 30 μg of protein. Protein bands were visualized by staining with Coomassie blue.

High Pressure Liquid Chromatography

The samples were analyzed on a YMC-Pack-300, S-5 um, 30 nm column (300×6 mm ID) using 100 mM sodium phosphate, pH 8.0+0.2 M NaCl as the liquid phase. The column was calibrated using gel filtration standards from Bio-Rad; thyroglobulin (7.2 min), gamma globulin (8.9 min), ovalbumin (9.67 min), myoglobin (10.46 min), and vitamin B12 (11.41 min).

Physical Properties

Figure 4:
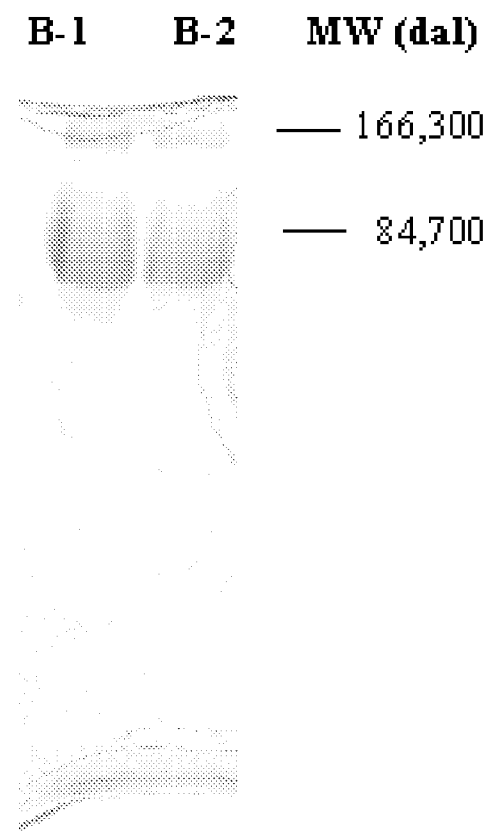
FIG. 4 is a photograph of a 10% SDS-PAGE of HuBChE purified from Cohn Fraction IV-4.

The purity of the HuBChE preparations can be followed by specific activity, evidence of a single protein band on SDS-PAGE and HPLC. The specific activity of the purified enzyme was about 700 U/mg measured in 50 mM sodium phosphate buffer at pH 8.0 at 25° C., using 1 mM butyrylthiocholine as the substrate. Active-site titration of purified enzyme with 7-(O, O-diethylphosphinyloxy)-1-methylquinolinium methyl sulfate (DEPQ) revealed that 1 mg of enzyme contains 11 nmoles of active-sites. Each nmole of enzyme contains 64 to 68 U of activity. The enzyme migrates as a single band on a reducing SDS-PAGE, with a subunit molecular weight of 85 kD as shown in FIG. 4. The size of the band is reduced to 65 kD upon treatment with N-glycosidase F. The intact protein migrates as a single band on native polyacrylamide gel electrophoresis, which can be stained for enzyme activity. The intact protein also migrates as a single peak on sucrose density gradients, with a sedimentation coefficient ($s_{20,w}$) of 12.44, corresponding to the tetrameric form of the enzyme. Similarly, the enzyme elutes as a single peak at 7.42 minutes from a YMC-Pack-300 column. us, the present invention provides an HuBChE preparation having 11 nmoles of active-sites per 1 mg and about 64 to about 68 U of activity per 1 nmole of enzyme.

In Vitro Stability

Figure 5:
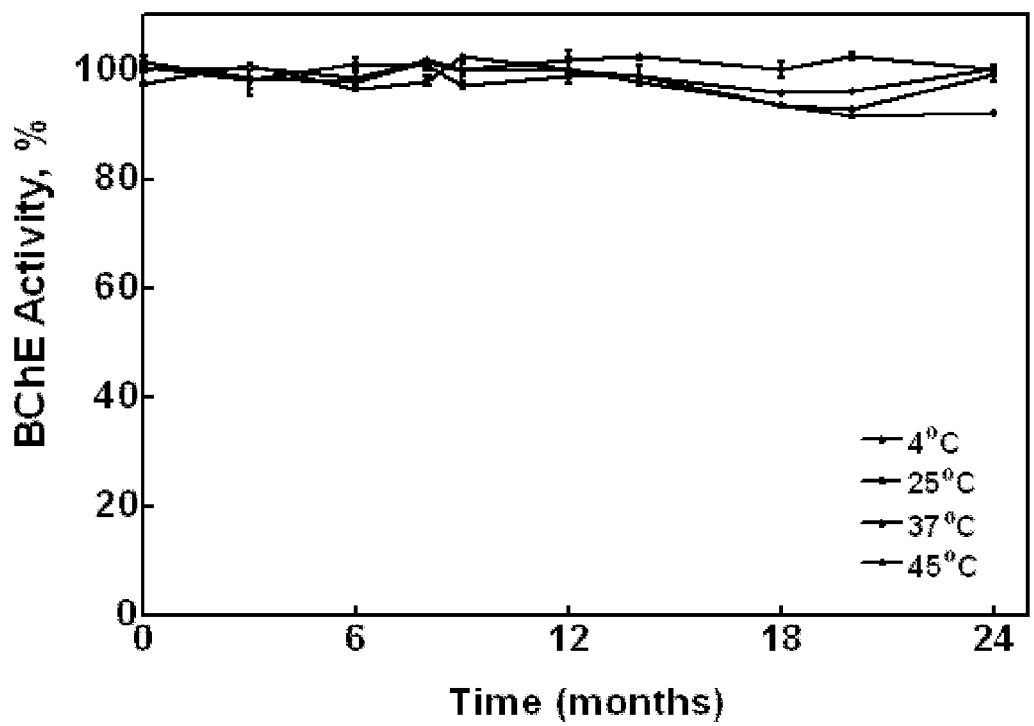
FIG. 5 is a graph depicting the thermal stability of HuBChE stored at various temperatures, in lyophilized form. Aliquots of enzyme (1 mg) were stored in lyophilized form at 4° C. (■), 25° C. (▲), 37° C. (▼) or 45° C. (●).

The stability of the HuBChE preparations at different storage temperatures was examined. Aliquots of the HuBChE preparations in lyophilized (1 mg) or liquid form (10 mg/ml in 50 mM sodium phosphate, pH 8.0+10% glycerol+1 mM EDTA) were stored at 4° C., 25° C., 37° C. or 45° C., and the enzyme activity. Samples were resuspended in 1 ml of 50 mM sodium phosphate buffer, pH 8.0 at various time intervals and assayed for BChE activity using the Ellman assay known in the art. The HuBChE preparations were found to be stable when stored in lyophilized from at 4° C., 25° C., 37° C. or 45° C. for over two years as shown in FIG. 5.

In Vivo Stability

The in vivo circulatory stability of the BChE of the HuBChE preparations was determined by measuring the pharmacokinetic profile of the enzyme (stored as lyophilized HuBChE preparations at −20° C. for various time periods) following i.m. administration into CD-1 mice as described below. The pharmacokinetic properties of the enzyme were not affected upon storage at −20° C. for at least 2 years. In other words, the pharmacokinetic properties of the HuBChE preparations do not show observable change when stored at −20° C. for about 2 or more years. Thus, the HuBChE preparations of the present invention are storage stable. A summary of the results is found in Table 2 as follows:

TABLE 2

In vivo Stability of HuBChE in Mice

| Parameters | Time of storage at −20° C. (months) | | | |
|---|---|---|---|---|
| | 3 | 10 | 17 | 25 |
| MRT (h) | 50.2 ± 3.2 | 55.2 ± 0.9 | 50.5 ± 1.4 | 49.3 ± 0.8 |
| $T_{1/2}$ (h) | 16.3 ± 0.4 | 17.9 ± 0.5 | 24.0 ± 2.4 | 15.9 ± 0.1 |
| $T_{max}$ (h) | 24 | 24 | 24 | 24 |
| $C_{max}$ (U/ml) | 10.1 ± 0.5 | 11.6 ± 0.4 | 17.7 ± 0.6 | 20.6 ± 0.8 |
| AUC | 754 ± 44 | 806 ± 25 | 1,216 ± 35 | 1,411 ± 20 |

Pharmacokinetics and Bioavailability

The following studies describe the pharmacokinetics and bioavailability of HuBChE from the HuBChE preparations in rodents and non-human primates. The results are summarized in Table 3 as follows:

TABLE 3

Pharmacokinetic Properties and Bioavailability

| Parameters | Monkeys 30 mg/kg | | Guinea Pigs 60 mg/kg | | Mice 30 mg/kg | |
|---|---|---|---|---|---|---|
| | i.v. | i.m. | i.p. | i.m. | i.p. | i.m. |
| MRT (h) | 72 ± 7 | NR | 109 ± 6 | 110 ± 4 | 42 ± 3 | 51 ± 2 |
| $T_{1/2}$ (h) | 36 ± 7 | 74 ± 4 | 63 ± 7 | 62 ± 4 | 11 ± 1 | 16 ± 1 |
| $T_{max}$ (h) | 0 | 10 ± 1 | 30 ± 2 | 27 ± 2 | 14 ± 5 | 24 ± 0 |

TABLE 3-continued

Pharmacokinetic Properties and Bioavailability

| Parameters | Monkeys 30 mg/kg | | Guinea Pigs 60 mg/kg | | Mice 30 mg/kg | |
|---|---|---|---|---|---|---|
| | i.v. | i.m. | i.p. | i.m. | i.p. | i.m. |
| $C_{max}$ (U/ml) | 222 ± 24 | 33 ± 6 | 293 ± 12 | 258 ± 12 | 364 ± 51 | 225 ± 23 |
| AUC (U/ml) × h | 16,538 ± 2,155 | 3,822 ± 133 | 39,163 ± 1,714 | 35,196 ± 2,084 | 20,279 ± 1,428 | 16,162 ± 1,258 |

1. Mice

Several doses of the HuBChE preparations (70 to 2100 HuBChE U/mouse, about 3 to 90 mg/kg) were administered into CD-1 mice by a single i.p. or i.m. injection. Blood samples were taken at 12 time points for up to 14 days post-injection for the measurement of blood BChE activity using the Ellman assay. The following pharmacokinetic parameters were determined from the time course curve of blood BChE concentration by using a Windows-based program for non-compartmental analysis of pharmacokinetic data: mean retention time (MRT), maximal concentration ($C_{max}$), time to reach the maximal concentration ($T_{max}$), elimination half-life ($T_{1/2}$), and area under plasma concentration time curve extrapolated to infinity (AUC). See Laub & Gallo (1996) *J. Pharmacol. Sci.* 85:393-395, which is herein incorporated by reference.

Blood BChE activity showed a rapid increase following i.p. injection and reached peak levels at about 10 hours. On the other hand, when the enzyme was delivered by i.m. injections, peak levels of activity were attained at about 24 hours. Regardless of the dose and route of administration, the enzyme displayed a MRT of 45 to 54 hours and $T_{1/2}$ of about 24 hours. Regardless of the dose administered, all exogenous HuBChE was completely cleared from the circulation of mice in 5 days.

2. Guinea Pigs a. Two doses of the HuBChE preparations (19.9 HuBChE mg/kg and 32.5 mg/kg) were injected i.m. in guinea pigs to determine its pharmacokinetics in blood. Mean whole blood HuBChE time-concentration data were fit to standard pharmacokinetic models. The pharmacokinetics of HuBChE in guinea pigs followed a one-compartment model with a single elimination phase.

b. The HuBChE preparations (60 mg/kg HuBChE) were administered to guinea pigs by a single i.p. or i.m. injection. Blood samples were taken for up to 14 days post-injection for the measurement of blood BChE activity. The HuBChE in the HuBChE preparations exhibited a marked prolonged MRT of about 110 hours in guinea pigs, which was at least twice as long as in mice. Guinea pigs still displayed 8 to 12 U/ml of HuBChE activity in blood at 14 days post administration.

3. Monkeys a. Two doses of the HuBChE preparations (5.25 HuBChE mg/kg and 8.75 mg/kg) were injected i.m. in cynomolgus monkeys to determine its pharmacokinetics in blood. The pharmacokinetics of HuBChE in cynomolgus monkeys also fit a one-compartment model with a single elimination phase.

b. The HuBChE preparations (30 HuBChE mg/kg) were administered in four rhesus monkeys by an i.v. bolus injection. At 5 minutes post-injection, the mean level of BChE in the blood was 226 U/ml. The mean residence time was about 72 hours. The HuBChE activity returned to baseline levels at 2 weeks post injection.

Safety and Toxicity

The following studies describe the safety and toxicity studies of HuBChE preparations in rodents and non-human primates.

1. Mice

Several doses of HuBChE preparations (70 to 2100 HuBChE U/mouse) were administered into CD-1 mice by a single i.p. or i.m. injection, as described above. Two weeks post-injection, all animals were euthanized and blood was collected for the analysis of multiple serum chemistry parameters (including glucose, urea nitrogen, creatinin, Na, K, Cl, $CO_2$, Ca, PHOS, cholesterol, total protein, triglycerides, albumin, AST, ALT, LDH, CK, ALKP, GGT, and total bili) and hematology parameters (including WBC, RBC, HGB, HCT, MCV, MCH, MCHC, RDW, PLT, MPV). Tissues were removed for complete gross/histopathological examination to determine any potential toxicity in vital organ and system functions. No toxic side effects were suggested from any of these observed parameters.

2. Guinea Pigs

The HuBChE preparations (60 HuBChE mg/kg) were administered to guinea pigs by a single i.p. or i.m. injection, as described above. Fourteen days post HuBChE injection, 20 panel serum chemistry, hematology, and complete gross/histopathology were examined in all animals. No toxic effects were found from these observed parameters.

3. Rhesus Monkeys

The HuBChE preparations (about 30 HuBChE mg/kg) were given to each of four Rhesus monkeys by an i.v. bolus injection to determine the behavioral and physiological safety of the preparations using a complex cognitive test (Serial-Probe Recognition, SPR) designed to assess attention and short-term memory known in the art. Blood samples were taken at various time intervals for 4 weeks post-injection for the measurement of blood BChE activity, anti-BChE (antibody) production, serum chemistry, and hematology tests. No cognitive-behavioral decrements of any kind were detected in SPR performance tests and no robust or consistent signs of clinical pathology were detected in any of the blood assays during the 5 weeks of observation.

Efficacy Studies

The following studies describe the efficacy studies of the HuBChE preparations in rodents and non-human primates. The results are summarized in Table 4 as follows:

TABLE 4

Protection against Organophosphate Nerve Agent Poisoning by HuBChE

| Agent | Species | Cumulative Dose ($LD_{50}$) | Recovery |
|---|---|---|---|
| GD | Guinea pig | 5.5 | Immediate (10 of 10) |

TABLE 4-continued

Protection against Organophosphate Nerve Agent Poisoning by HuBChE

| Agent | Species | Cumulative Dose ($LD_{50}$) | Recovery |
|---|---|---|---|
| VX | Guinea pig | 5.0 | Immediate (9 of 9) |
| GD | Cynomolgus monkey | 5.5 | 4 of 6[1] |

[1] Of the six animals given Hu BChE, one died within 10 min after the third dose of GD; another animal survived for 48 h (experimental criteria) but was euthanized on recommendation of the attending veterinarian. The remaining animals survived with no signs of intoxication have been symptom free for about 20 months.

1. Guinea Pigs

Guinea pigs were pretreated with a HuBChE preparation by a single i.m. injection to provide HuBChE in a sufficient quantity to neutralize a total challenge of 8 to 9×$LD_{50}$ of soman (1×$LD_{50}$=30 μg/kg s.c. or VX (1×$LD_{50}$=9 μg/kg s.c.), respectively. At 18±1 hour post administration, blood samples were withdrawn for the determination of BChE concentration. The total number of moles of HuBChE available in circulation was calculated by assuming a total blood volume of 20 ml for a 400 g guinea pig. Agent doses were about 1.5, 2.0 and 2.0×$LD_{50}$ administered s.c. 90 to 120 minutes apart for a total exposure of 5 to 6×$LD_{50}$. All animals (n=10) survived soman challenge without any observable toxic signs. A complete necropsy and histopathology performed at 7 days (n=5) or 14 days (n=5) post soman challenge revealed no abnormal finding in any samples. Animals were challenged with VX under the same paradigm as used for soman experiments, except that agent doses were about 2.0, 2.0 and 1.0× $LD_{50}$ administered s.c. 90 to 120 minutes apart for a total exposure of 5×$LD_{50}$. All animals (n=9) survived VX challenge without any observable toxic signs. A complete necropsy and histopathology performed at 7 days (n=5) or 14 days (n=5) post VX challenge revealed no abnormal finding in any samples. None of the animals in either challenge group received therapy in the form atropine, 2-PAM or diazepam.

3. Cynomolgus Monkeys

Six cynomolgus monkeys were pretreated with HuBChE preparations (24.1 mg/kg of HuBChE) by a single i.m. injection and challenged at $T_{max}$ with three doses of soman. A total 5.5×$LD_{50}$ of soman were administered sequentially using a dose of 1.5, 2.0 and 2.0×$LD_{50}$, given 90 to 120 minutes apart. None of the animals displayed signs of OP intoxication following the first two doses of soman (a cumulative challenge of 3.5×$LD_{50}$). After the third challenge dose, one animal died within 1 hour and the second one was euthanized at 48 hours because of its moribund condition. The four animals were monitored for long-term health effects by analysis of serum chemistry and hematology parameters for 20 months. No OP toxicity or any other kind of toxicity was observed after more than twenty months. These results also demonstrate that HuBChE irreversibly inhibited by soman is not toxic to animals.

As provided herein, the HuBChE preparations of the present invention may be used as a prophylactic treatment which may be advantageously administered as a single pretreatment capable of protecting against multiple $LD_{50}$'s of a wide variety of potent OP agents without the requirement of additional post-exposure therapy. In some embodiments, the HuBChE preparations according to the present invention can be packaged as storage stable single dose. The single doses may be packaged as prefilled syringes or autoinjectors. In addition to treating or preventing OP toxicity, the HuBChE preparations according to the present invention may be used to hydrolyze cocaine, succinylcholine, mivacurium, albuterol, and the like. Therefore, the HuBChE preparations of the present invention can be used for alleviating toxicity due to overdosing of these drugs.

As disclosed herein, the present invention provides a process for the large-scale manufacture of human butyrylcholinesterase (HuBChE) from Cohn Fraction IV-4 paste. Three small-scale purifications were performed to evaluate the proposed manufacturing process. Following this, two large-scale purification runs were performed using 80 kg of Fraction IV-4 paste. A total of 9.4 million units of HuBChE were produced with a purity of about 99%, for the two runs. Both the yield and purity met or exceeded expectations for pre-clinical material. Based on the successful results of this study, a manufacturing procedure has been developed that is suitable for the pre-clinical production of HuBChE.

As provided herein, 5 development runs were conducted. The first three runs were small-scale runs utilizing about 800 grams of Cohn Fraction IV-4 paste starting material. The final two runs were performed at the 80 kilogram scale and were intended to produce HuBChE for preclinical experiments. Refinements include using chromatography gels in columns as opposed to the batch method, using a gradient for DEAE column elution, the introduction the Cohn Fraction IV-5 process, and the introduction of centrifugation for clarification.

Small Scale Procedure

Three small-scale purifications were performed. The first study attempted to use filtration as the primary clarification method. Runs #2 and #3 utilized centrifugation as the primary clarification method. A summary of the major process steps and the parameters evaluated for each step are presented below. Note: All manufacturing steps were performed at 2° C. to 8° C. in a cold room or in tempered process vessels.

Study #1

Resuspension: A total of 800 g of Cohn Fraction IV-4 paste (PN 527BE, Batch 02ZB005) was resuspended in 7200 g of 25 mM sodium phosphate, 1 mM EDTA, pH 8.0 (EQ Buffer) at room temperature. The resuspension was mixed for 17.5 hours at 2° C. to 8° C.

Depth Filtration: A Cuno® Biocap 1000 60LA filter capsule was flushed with 3 L of water. Acid washed Celite® 521 (5 g) was added to 5.5 L of EQ Buffer and flushed through the capsule to precoat the filter. Acid washed Celite® 521 was added to the product at a rate of 20 g/kg of resuspension (160 g total) and mixed for 30 minutes. Filtration was started at 110 ml/min. The flow rates rapidly declined necessitating filter replacement. Although a total of three filters were used, the entire product volume could not be filtered. The final filtered volume was about 10 L (including EQ buffer flushes). About 2 L of unfiltered product was discarded.

Membrane Filtration: The Cuno® filtrate was filtered through one 1.2 μm Pall HDC II cartridge. It was then filtered through two 47 mm 0.65 μm Millipore® Durapore filter discs.

Procainamide Chromatography: A column (Pharmacia K50/30) was previously packed with new unused procainamide sepharose to a bed height of 12 cm (volume=240 ml). The packing flow rate was about 20 ml/min (about 1 cm/min linear flow rate). The column was pre-cycled with EQ Buffer (about 10 CV), 2.0 M NaCl (about 3 CV), DI water (about 1.2 CV), 0.5 M HAc (about 1.4 CV), DI water (about 1 CV), and EQ Buffer (about 4 CV). Flow rates ranged from 1 ml/min to 7 ml/min determined by convenience. Filtered product was loaded onto the column at flow rates between 6.5 ml/min and 7.7 ml/min. Overall loading time was 24 hours 40 minutes. No plugging or signs of high pressure were observed. The column was washed with EQ Buffer at 6.3 ml/min for about 6 CVs. After reversing the direction of flow direction, the column was washed with EQ Buffer+0.05 M NaCl at 7.6 ml/min for about 38 CVs. The column turned a bright blue during this step, due to the presence of bound ceruloplasmin. Elution was performed with EQ Buffer+1.0 M NaCl at a flow rate of 7.6 ml/min. Fractions (about 8.7 ml/fraction) were collected using a fraction collector. A total of 195 ml of product was pooled for further processing.

Diafiltration: A Millipore® stirred cell diafiltration apparatus was assembled with a Millipore® 100 kD (YM100) membrane. The product was diafiltered with about 5× volumes of water and concentrated to a final volume of 125 ml.

pH Adjustment: The pH of the diafiltered pool was adjusted from 8.05 to 4.94 by the addition of 2.5 ml of 1 M NaAc pH 4.09. The pH was then adjusted to 4.02 by the addition of about 0.4 ml of HAc.

Filtration: The product was filtered through a 1.2 µm membrane filter.

Solvent/Detergent Treatment: S/D was prepared by mixing 5.81 g of 20% Triton X-100 with 0.33 g of TNBP. The S/D was added to the filtered product and mixed overnight at 2° C. to 8° C.

DEAE Chromatography: A column (Pharmacia K50/30) was previously packed with new unused DEAE sepharose fast flow to a bed height of 11 cm (volume=220 ml). The packing flow rate was about 12 ml/min (about 0.6 cm/min linear flow rate). The column was washed extensively with 20 mM NaAc pH 4.0 buffer (>17 CVs). Product was loaded onto the column at a flow rate of 2 ml/min. Overall loading time was about one hour. The column was washed with 20 mM NaAc pH 4.0 buffer at 2 ml/min for about 1.6 CVs and then at 4 ml/min for 1.1 CVs. The column was then washed with 20 mM NaAc pH 4.0 buffer+0.05 M NaCl at 4.0 ml/min for about 18 CVs. Elution was performed with EQ Buffer+0.2 M NaCl at a flow rate of 3.7 ml/min. Fractions (about 7.4 ml/fraction) were collected using a fraction collector. A total of 59 ml of product was pooled. The column was cleaned by use of 1.5 CVs of 2.0 M NaCl and stored in 20% (v/v) ethanol.

Diafiltration: A Millipore stirred cell diafiltration apparatus was assembled with a Millipore 100 kD membrane. The product was concentrated to 25 ml and then diafiltered with about 5× volumes of EQ Buffer. Product was concentrated to a final volume of 15 ml.

Study #2

Resuspension: A total of 800 g of Cohn Fraction IV-4 paste (PN 527BE, Batch 02ZB005) was resuspended in 7200 g of water at room temperature. The resuspension was mixed for about 7 hours at 2° C. to 8° C.

pH Adjustment: The pH of the resuspension was adjusted to 4.90 by the addition of 80×NaAc.

Centrifugation: The resuspension was centrifuged using a Sorvall® RC5B refrigerated centrifuge with a GS3 rotor at 9000 rpm (15000×g) for 8 minutes. The final supernatant volume was 7750 ml.

Depth Filtration: A Cuno® Biocap 1000 60LA filter capsule was flushed with 3 L of water followed by 10 L of 20 mM NaAc, pH 4.9. Acid washed Celite® 521 was added to the product at a rate of 4 g/kg of product (31 g total) and mixed for 33 minutes. The total product volume was filtered through one filter. The final filtered volume (including buffer chase) was about 12.5 L.

pH Adjustment: The product pH was adjusted to 8.0 by the addition of about 566 ml of 1 M NaOH solution. The final volume was about 13 L.

Membrane Filtration: The product was filtered through one 1.2 µm Pall HDC II cartridge. This was followed by 0.65 µm Millipore® Durapore filtration (two 47 mm discs were required).

Procainamide Chromatography: Additional procainamide sepharose gel was added to the column (from Study #1) and repacked to a bed height of 15.5 cm (CV=300 ml). Product was loaded onto the column at about 8 ml/min with a total loading time of about 27 hours. No plugging or signs of high pressure were observed. The column was washed with EQ Buffer at about 8 ml/min for about 5.2 CVs. The column was then washed with EQ Buffer+0.05 M NaCl at about 8.0 to 8.5 ml/min for about 11 CVs. At this time the flow rate was reduced to 2 ml/min and the wash continued for about another 32 CVs. Elution was performed with EQ Buffer+0.5 M NaCl at a flow rate of 5.3 ml/min. Fractions (about 8 ml) were collected using a fraction collector. A total of 271.5 ml of product was pooled for further processing.

Diafiltration: A Millipore® stirred cell diafiltration apparatus was assembled with a Millipore 100 kD membrane. The product was diafiltered with at least 5× volumes of EQ Buffer and concentrated to a final volume of about 112 ml.

DEAE Chromatography: The DEAE column was equilibrated with EQ Buffer. Product was loaded onto the column at a flow rate of 3 ml/min. Following loading, the column was washed with about 1.4 CVs of EQ Buffer at 3 ml/min. After reversing the direction of flow of the column the column was washed with EQ Buffer+0.05 M NaCl at 2.0 ml/min for about 17.5 CVs. Elution was performed with EQ Buffer+0.2 M NaCl at a flow rate of 3.0 ml/min. Fractions (about 7.5 ml) were collected using a fraction collector. A total of 94 ml of product was pooled.

Study #3

Resuspension: A total of 801 g of Cohn Fraction IV-4 paste (PN 527BE, Batch 02ZB005) was resuspended in 7201 g of water at room temperature. The resuspension was mixed for about 7 hours at 2° C. to 8° C.

pH Adjustment: The pH of the resuspension was adjusted to 4.9 by the addition of 80×NaAc.

Centrifugation: The resuspension was centrifuged using a Sorvall® RC5B refrigerated centrifuge at 9000 rpm (15000× g) for 8 minutes. The final supernatant volume was 7452 ml.

Depth Filtration: A Cuno® Biocap 1000 60LA filter capsule was flushed with 5 L of water followed by 5 L of 20 mM NaAc, pH 4.9. Acid washed Celite® 521 was added to the product at a rate of 4 g/kg of product (30 g total) and mixed for 43 minutes. The product was filtered through one Cuno® filter. A final filtrate volume (including buffer chase) was 9525 g.

pH Adjustment: The product pH was adjusted to 8.0 by the addition of 470 ml of 1 M NaOH solution. The final volume was about 9950 ml.

Membrane Filtration: The product was filtered through a 1.2 µm Pall HDC II cartridge. This was followed by 0.65 µm Millipore® Durapore filtration.

Procainamide Chromatography: Product was loaded onto the procainamide sepharose column at about 6.8 to 7.0 ml/min. No plugging or signs of high pressure were observed. The column was washed with EQ Buffer at about 6.5 ml/min for about 9.9 CVs. The column was then washed with EQ Buffer+0.05 M NaCl at about 1.1 ml/min for about 75 CVs. Elution was performed with EQ Buffer+0.5 M NaCl at a flow rate of 5.0 ml/min. Fractions (about 7.5 ml) were collected using a fraction collector. A total of 187 g (about 187 ml) of product was pooled for further processing.

Diafiltration: A Millipore® stirred cell diafiltration apparatus was assembled with a Millipore® 100 kD membrane. The product was diafiltered with at least 5× volumes of EQ Buffer and concentrated to a final volume of about 95 ml.

DEAE Chromatography: The DEAE column was equilibrated with EQ Buffer. Product was loaded onto the column at a flow rate of 2.5 ml/min. and followed by a 4.1 CV wash with EQ Buffer at 2.5 ml/min. The column was then washed with EQ Buffer+0.05 M NaCl at 1.0 ml/min for 30.5 CVs. Elution was performed with EQ Buffer+0.2 M NaCl at a flow rate of 3.0 ml/min. Fractions (about 7.5 ml) were collected using a fraction collector. A total of 65 ml of product was pooled.

Large Scale Procedure

Two large-scale pre-clinical production runs were performed using 80 kg of Cohn Fraction IV-4 paste for each run. Based on the small-scale runs, a draft Master Production Record (MPR) was prepared and used to record the manufacturing data. The following is a summary of the production runs.

Pre-Clinical Run #1

Resuspension: A total of 81.5 kg of Cohn Fraction IV-4 paste (PN 527BE, Batch Nos. 02ZB002 and 02ZB007) were resuspended in 738 kg of CWFI. The resuspension was mixed for 6 hours 50 minutes at 0° C. to 4° C.

pH Adjustment: The pH of the resuspension was adjusted to 4.90 by the addition of 1.91 kg of 80× concentrated NaAc buffer.

Centrifugation: The Cohn Fraction IV-4 resuspension was centrifuged in the Carr P18 Powerfuge at 7663 rpm at a feed flow rate of 4.0 kg/min. This resulted in 712 kg of supernatant and 16.8 kg of paste.

Depth Filtration: Three Cuno® 60LA filter cartridges were installed in a Cuno® filter housing and flushed with 100 kg of water. A total of 0.75 kg of acid washed Celite® 521 was added to 498 kg of CWFI and mixed for 30 minutes. This mixture was then transferred through the Cuno® filters to precoat the filter surface. This was followed by a 200 kg rinse with 20 mM NaAc, pH 4.9 buffer. A total of 2.85 kg of acid washed Celite® 521 was added to the 712 kg of product and mixed for about one hour. (4 g Filter Aid/kg of product). The product was then filtered through the Cuno® filters. Following filtration the housing was chased with buffer to recover additional product. The final filtered volume (including buffer chase) was 963 L.

pH Adjustment: The product was adjusted to pH 8.04 by the addition of 50.34 kg of 0.4 N NaOH solution. This resulted in 1016 kg of product.

Membrane Filtration: The product was filtered through a 30 inch 0.65 μm filter cartridge (Millipore® Durapore CVDR73TP3). Final quantity after filtration was 1005 kg.

Procainamide Chromatography: Procainamide sepharose gel was packed into a Amicon P630 X 500 column to a bed height of 8.5 cm (CV=26.5 L). The column was equilibrated with a minimum of 5 CVs of EQ buffer. Product was loaded onto the column at about 1100 ml/min with a total loading time of about 16 hours. No plugging or signs of high pressure were observed. The column was washed with 134 kg (5 CVs) EQ Buffer at 1100 ml/min. The column was then washed with 1441 kg (54 CVs) EQ Buffer +0.075 M NaCl at about 155 ml/min or 0.35 minutes per milliliter of column volume. This required about 163 hours (6.8 days) or 0.37 minutes per milliliter of column volume processing time. Elution was performed with EQ Buffer+0.5 M NaCl at a flow rate of 800 ml/min. A total of 33 fractions (about 800 ml each) were collected manually corresponding to the protein peak (as determined by A280). Fractions 4 through 22 were pooled for further processing. It was later discovered that significant activity was present in the column regeneration fractions 34 and 35. Since these fractions showed good purity they were retained for further processing. Fractions 23 through 33 also contained relatively pure BuChE and were retained. The overall recovery totaled 87 liters of column effluent representing about 8.4 million units of activity.

Diafiltration: A Pellicon® apparatus was assembled with 1.0 m² of 100 kD membranes (Millipore® PN: P2C100C05). The unit was washed with WFI and EQ buffer prior to use. The initial product pool (fractions 4 to 22) was concentrated to 9.82 kg and then diafiltered with 13× volumes of EQ Buffer. The final volume was 11.96 L. Later, pooled fractions 23 to 33 were concentrated and diafiltered yielding 4.3 kg. Finally fractions 34 and 35 were individually processed yielding 9.32 kg and 6.65 kg respectively. Concentrated diafiltered product resulting from fractions 23 to 35 were pooled together for further processing.

DEAE Chromatography: DEAE sepharose fast flow gel was packed into a Millipore VA250 X 500 column to a bed height of 37.9 cm (CV=18.6 L). The column was equilibrated with a minimum of 5 CVs of EQ Buffer. Concentrated diafiltered product from fractions 4 to 23 was loaded onto the column at a flow rate of 75 ml/min. Following loading, the column was washed with about 3 CVs (58.2 kg) of EQ buffer at 75 ml/min. The column was then washed with EQ Buffer+0.05 M NaCl at 75 ml/min for about 4.7 CVs. At this point a decision was made that the concentrated diafiltered pools from fractions 23 to 35 would also be loaded onto this column. The EQ Buffer+0.05 M NaCl wash was terminated and the column was re-equilibrated with 5 CVs of EQ buffer. The second product pool, representing fractions 23 to 35, was loaded onto the column at a flow rate of 75 ml/min. After completion of loading, the column was washed with about 3 CVs of EQ buffer at 75 ml/min. The column was then washed with EQ Buffer+0.05 M NaCl at 75 ml/min for about 41 CVs. The column was eluted with a 10 CV gradient from EQ Buffer+0.05 M NaCl (low) to EQ Buffer+0.3 M NaCl (high) at a flow rate of 75 ml/min. Fractions of 500 ml were collected manually starting at the appearance of protein as detected by a flow through UV monitor at $A_{280}$. A total of 24 fractions (#3 to #26), totaling 25.25 kg of product, were pooled for further processing. Following regeneration with about 4 CV of EQ+2.0 M NaCl buffer, the column was stored in 20% ethanol solution.

Diafiltration: A Millipore® Pellicon apparatus, with 1.0 m² of 100 kD membranes, was washed with WFI and EQ buffer prior to use. The DEAE product pool was concentrated to 5.15 kg and then diafiltered with EQ Buffer. An additional 1 liter of EQ buffer was recirculated through the Pellicon unit to recover additional product. This was repeated for a second 1 liter recirculation. The final volume of concentrated diafiltered product was 8.35 kg.

Pre-Clinical Run #2

Resuspension: A total of 80.0 kg of Cohn Fraction IV-4 paste (PN 527BE, Batch Nos. 02ZB004, 02ZB005, and 02ZB008) were resuspended in 720 kg of CWFI. The resuspension was mixed for 6 hours at 0° C. to 4° C.

pH Adjustment: The pH of the resuspension was adjusted to 4.90 (from 5.73) by the addition of 1.58 kg of 80× concentrated NaAc buffer.

Centrifugation: The Cohn Fraction IV-4 resuspension was centrifuged in the Carr P18 Powerfuge at 7663 rpm at a feed flow rate of 4.0 kg/min. Temperature was maintained at 2° C. to 8° C. This resulted in 712 kg of supernatant and 17.2 kg of paste.

Depth Filtration: Three Cuno® 60LA filter cartridges were installed in a Cuno® filter housing and flushed with 102 kg of water. A total of 0.75 kg of acid washed Celite® 521 was added to about 438 kg of CWFI and mixed for 30 minutes. This mixture was then transferred through the Cuno® filters to precoat the filter surface. This was followed by a 200 kg rinse with 20 mM NaAc, pH 4.9 buffer. A total of 2.85 kg of acid washed Celite® 521 was added to the 712 kg of product and mixed for about one hour (4 g Filter Aid/kg of product). The product was then filtered through the Cuno® filters. Following filtration the housing was chased with buffer to recover additional product. The final filtered volume (including buffer chase) was 963 L.

pH Adjustment: The product was adjusted to pH 7.95 by the addition of 29.78 kg of 0.4 N NaOH solution. This resulted in 883 kg of product.

Membrane Filtration: The product was filtered through a 30 inch 0.65 μm filter cartridge. Final quantity after filtration was 839 kg.

Procainamide Chromatography: The procainamide sepharose column was equilibrated with a minimum of 5 CVs of EQ buffer. Product was loaded onto the column at about 1100 ml/min with a total loading time of about 13 hours 10 minutes. No plugging or signs of high pressure were observed. The column was washed with 144.2 kg (5.4 CVs) EQ Buffer at 1100 ml/min. The column was then washed with 2242 kg (84 CVs) EQ Buffer+0.075 M NaCl at about 155 ml/min or 0.54 minutes per milliliter of column volume. This required about 250.7 hours (10.4 days). Elution was performed with EQ Buffer+1.0 M NaCl at a flow rate of 800 ml/min. Due to an error in setting up the UV monitor, the start of the protein peak was not detected. Fraction collection was started as soon as the error was discovered. The "missed" portion of the peak was collected in Fraction 1 along with the column void volume (32.1 kg). Fortunately, no material was lost as a result of this error. The pool totaled 53.2 kg representing about 6.4 millions unity of activity. The column was regenerated with at least 4 CV of EQ+2.0 M NaCl.

Diafiltration: A Millipore® Pellicon apparatus, with 1.0 m² of Millipore 100 kD membranes, was washed with WFI and EQ buffer prior to use. The Procainamide pool was concentrated to 10.72 kg and then diafiltered with more than 16× volumes of EQ Buffer. The final diafiltered volume was 12.4 L.

DEAE Chromatography: The DEAE column was equilibrated with a minimum of 5 CVs of EQ Buffer. Diafiltered product was loaded onto the column at a flow rate of 75 ml/min. Following loading, the column was washed with about 3.3 CVs (60.4 kg) of EQ buffer at 75 ml/min. The column was then washed with EQ Buffer+0.05 M NaCl at 75 ml/min for about 77 CVs. This required about 269 hours (11.2 days). The column was eluted with a 10 CV gradient from EQ Buffer+0.05 M NaCl (low) to EQ Buffer+0.3 M NaCl (high) at a flow rate of 75 ml/min. Fractions of 1000 ml were collected manually starting at the first appearance of protein as detected by a flow through UV monitor at $A_{280}$. A total of 16 fractions (#7 to #22), totaling 16.75 kg of product, were pooled for further processing. The column was regenerated with about 4 CV of EQ+2.0 M NaCl Buffer. The column was stored in 20% ethanol solution.

Diafiltration: A Millipore® Pellicon apparatus, assembled with 1.0 m² of Millipore 100 kD membranes, was washed with WFI and EQ buffer prior to use. The DEAE product was concentrated to 4.75 kg and then diafiltered with 8.6× volumes of EQ Buffer. An additional 1 liter of EQ buffer was recirculated through the Pellicon unit to recover additional product. This was repeated for a second 1 liter recirculation. The final volume of concentrated diafiltered product was 7.8 kg.

Results

Small-Scale Runs

Table 5 is a summary of the studies that were performed during development followed by the reasons for the modifications.

TABLE 5

Fraction IV-4 Paste Resuspension

| | Fr. IV-4 Paste | | Solvent | | | Mixing | |
|---|---|---|---|---|---|---|---|
| Run # | Lot # | Wt. (g) | Type | Vol (ml) | pH | Time (hr) | Temp (° C.) |
| 1 | 02ZB005 | 800 | EQ Buffer | 7200 | 8.0 | 17.5 | 2-8 |
| 2 | 02ZB005 | 800 | CWFI | 7200 | NA | 7 | 2-8 |
| 3 | 02ZB005 | 801 | CWFI | 7201 | NA | 7 | 2-8 |

Resuspension, pH adjustment, and clarification: Cohn Fraction IV-4 paste was resuspended in EQ Buffer at pH 8.0. Filter aid was added and the mixture was filtered through the Cuno® 60 LA Biocap depth filter capsule. This proved difficult and required several capsules. Following Cuno® filtration, membrane filtration at 1.2 μm and 0.65 μm presented no problem. Since use of a filter press was not an option, it was decided to evaluate centrifugation as the bulk clarification method. It was also decided to evaluate combining the low pH adjustment step (performed prior to the DEAE column) with the resuspension and centrifugation steps. As a result, the paste was resuspended in CWFI followed by adjustment to pH 4.9. This is the Cohn Fraction IV-5 method and was performed during small-scale Studies #2 and #3.

Centrifugation: Centrifugation removed sufficient quantities of solids so that the subsequent Cuno® filtration and membrane filtration steps were performed without difficulty. Previous studies indicated that BChE binding to the procainamide gel is greater at pH 8.0 than at pH 4.9. Therefore, the pH of the product was adjusted to pH 8.0 prior to loading onto the procainamide column (Runs #2 and #3).

Procainamide Chromatography: For the first run, the EQ+0.05 M NaCl wash and EQ+1.0 M NaCl elution was performed in the reverse direction relative to the load direction. For Runs #2 and #3, the elution buffer salt concentration was reduced from 1.0 M NaCl to 0.5 M NaCl in order to elute the product off the column but not other tighter binding contaminating proteins.

The three small-scale studies are summarized in Table 6.

TABLE 6

Procainamide Chromatography

| | | Load | | Post Flush | | Wash (EQ + 0.05 M NaCl) | | | Elution | |
|---|---|---|---|---|---|---|---|---|---|---|
| Run # | CV (ml) | FlowRate (ml/min) | Vol (L) | FlowRate (ml/min) | Vol (CV) | FlowRate (ml/min) | Vol (CV) | NaCl (M) | FlowRate (ml/min) | Vol (ml) |
| 1 | 240 | 6.5-7.7 | ~10 | 6.3 | 6 | 7.6* | 38 | 1.0 | 7.6* | 195 |
| 2 | 300 | 8.0 | ~13 | 8.0 | 5.2 | 8.0-8.5 2.0 | 11.3 31.6 | 0.5 | 5.3 | 271.5 |
| 3 | 300 | 6.8-7.2 | 9.95 | 6.5 | 9.9 | 1.1 | 75 | 0.5 | 5.0 | 187 |

*Flow in reverse direction

Diafiltration: All three lots were concentrated and diafiltered (at least about 5× volumes) using Millipore® 100 kD membranes in a stirred cell apparatus. The final concentrated and diafiltered volumes of 125 ml, 112 ml, and 95 ml were obtained for lots #1, #2, and #3 respectively.

pH Adjustment (Run #1 only): The pH of the product was adjusted from 8.05 to 4.02 by the addition of sodium acetate and acetic acid. The product was 1.2 μm filtered to remove any precipitate that might result from the pH adjustment.

Solvent Detergent Treatment (Run #1 only): Solvent detergent mixture was added to the product and mixed overnight before loading onto the DEAE column. The pooled product of the DEAE column was tested for the presence of Triton X-100. None was detected (<about 1.0 μg/ml).

DEAE Chromatography: For Run #2, the EQ+0.05 M NaCl wash and EQ+0.2 M NaCl elution was performed in the reverse direction relative to the load direction. For Run #3, the EQ+0.05 M NaCl wash was extended to 30.5 CVs in an attempt to increase purity of the final eluted product. Table 7 summarizes the DEAE chromatography.

TABLE 7

DEAE Chromatography

| | | Load | | Post Flush | | Wash (EQ + 0.05 M NaCl) | | | Elution | |
|---|---|---|---|---|---|---|---|---|---|---|
| Run # | CV (ml) | FlowRate (ml/min) | Vol (ml) | FlowRate (ml/min) | Vol (CV) | FlowRate (ml/min) | Vol (CV) | NaCl (M) | FlowRate (ml/min) | Vol (ml) |
| 1 | 220 | 2 | 116 | 2-4 | 2.7 | 4.0 | 18 | 0.2 | 3.7 | 59 |
| 2 | 220 | 3 | 112 | 3 | 1.4 | 2.0* | 17.5 | 0.2 | 3.0* | 94 |
| 3 | 220 | 2.5 | 95 | 2.5 | 4.1 | 1.0 | 30.5 | 0.2 | 3.0 | 65 |

*Flow in reverse direction

Diafiltration: All three lots were concentrated and diafiltered (≧about 5× volumes) using Millipore® 100 kD membranes in a Millipore stirred cell apparatus. The final concentrated and diafiltered volumes of 15 ml, 112 ml, and 95 ml were obtained for lots #1, #2, and #3 respectively.

Analytic Results: Recovery of BuChE activity is presented in Table 8.

TABLE 8

BuChE Recovery

| | Run #1 | | Run #2 | | Run #3 | |
|---|---|---|---|---|---|---|
| Step | Total Units | Recovery (%) | Total Units | Recovery (%) | Total Units | Recovery (%) |
| Resuspension | 103700 | 100 | 101000 | 100 | 89860 | 100 |
| pH Adjustment to 4.9 | na[1] | na[1] | 109500 | 108.5 | 111600 | 124.2 |
| Centrifugation | na[1] | Na[1] | 108100 | 107.1 | 99110 | 110.3 |
| Filter Aid Addition | 92750 | 89.5 | 110700 | 109.6 | 107500 | 119.6 |
| Depth Filtration | 60000 | 57.9 | 99500 | 98.6 | 106500 | 118.5 |
| pH Adjustment to 8.0 | na[1] | Na[1] | 97240 | 96.3 | 96950 | 107.9 |

TABLE 8-continued

| | BuChE Recovery | | | | | |
|---|---|---|---|---|---|---|
| | Run #1 | | Run #2 | | Run #3 | |
| Step | Total Units | Recovery (%) | Total Units | Recovery (%) | Total Units | Recovery (%) |
| 1.2 μm Filtration | 56600 | 54.6 | 96070 | 95.2 | 109800 | 122.2 |
| 0.65 μm Filtration | 57500 | 55.5 | 97760 | 96.8 | 97720 | 108.7 |
| Procainamide Column | 44460 | 42.9 | 59820 | 59.2 | 86260 | 96.0 |
| Diafiltration | 39000 | 37.6 | 60990 | 60.4 | 49530 | 55.1 |
| pH Adjustment to 4.0 | 35330 | 34.1 | na$^2$ | na$^2$ | na$^2$ | na$^2$ |
| 1.2 μm Filtration | 33480 | 32.3 | na$^2$ | na$^2$ | na$^2$ | na$^2$ |
| S/D Treatment @ 15 min$^3$ | 30040 | 29.0 | na$^3$ | na$^3$ | na$^3$ | na$^3$ |
| S/D Treatment @ 19 hr$^3$ | 25640 | 24.7 | na$^3$ | na$^3$ | na$^3$ | na$^3$ |
| DEAE Column | 16700 | 16.1 | 17720 | 17.5 | 50430 | 56.1 |
| Concentration | 15310 | 14.8 | No data | | | |

$^1$Small-scale Run #1 was clarified by depth filtration only. There was no pre or post filtration pH adjustment.
$^2$Adjustment to pH 4.0 was performed for Run #1 only. This step was followed by filtration to remove any precipitate.
$^3$Solvent Detergent treatment was performed on Run #1 only.

Total protein recovery in all the DEAE pools represented less than 0.1% of the total protein present at the resuspension step.

Large-Scale Runs

Resuspension: Both large-scale resuspensions were performed similarly and are summarized in Table 9.

TABLE 9

| | Fraction IV-4 Paste Resuspension | | | | | |
|---|---|---|---|---|---|---|
| | | | | | Mixing | |
| Run # | Fr. IV-4 Paste Lot # | Wt. (kg) | Solvent Type | Vol (kg) | Time (hr) | Temp (° C.) |
| 1 | 02ZB002 02ZB007 | 81.5 | CWFI | 738 | 6 hr 50 min | 0-4 |
| 2 | 02ZB004 02ZB005 02ZB008 | 80.0 | CWFI | 720 | 6 hr | 0-4 | pH Adjustment: The pH was adjusted to 4.9 by the addition of 80× Buffer (pH 4.0). The volumes of 80× Buffer required were 1.91 kg for Run #1 and 1.58 kg for Run #2.

Centrifugation: The two runs were performed similarly. Results are presented in Table 10 below.

TABLE 10

| | Centrifugation | | | | |
|---|---|---|---|---|---|
| | | Centrifugation | | Final Product | |
| Run # | Initial Wt (kg) | RPM | Feed Rate (kg/min) | Supernatant (kg) | Paste (kg) |
| 1 | ~821* | 7663** | 4.0-4.1 | 712 | 16.8 |
| 2 | 797 | 7663** | 4.0 | 712 | 17.2 |

*Problems with the tank's load cells prevented getting an accurate initial weight of the product.
**The effective centrifugal force at 7663 rpm is about 15,000 G (depending on how full the bowl is).

Temperatures were measured during the entire centrifugation process at the feed and centrate (discharge) locations as well as at the product destination tank. The results are presented in Table 11.

TABLE 11

| | Temperature Control During Centrifugation | | | | | |
|---|---|---|---|---|---|---|
| | Feed Temp (° C.) | | Centrate Temp (° C.) | | Destination Tank Temp (° C.) | |
| Run# | High | Low | High | Low | High | Low |
| 1 | 7.0 | 4.4 | 6.5 | 3.8 | 4.0 | 3.1 |
| 2 | 8.5 | 4.4 | 6.0 | 2.4 | 4.1 | 4.0 |

Depth Filtration: In Run #1, the product was filtered through one Cuno® housing containing three Zeta Plus 60LP filter cartridges representing 36 ft$^2$ of filter area. The filters in Run #2 plugged before the entire volume was filtered. It was necessary to direct the filtered material (Run #2a) back to the source tank and repeat the filtration step with a fresh set of filters (Run #2b). Filtration through the second set of filters in Run #2 also proved difficult. Some material was lost in the filter housing. The usage of filter aid (FA) is summarized in Table 12.

TABLE 12

| | Filter Aid Usage During Depth Filtration | | | | | |
|---|---|---|---|---|---|---|
| | | Filter Aid | | Filter Aid Body Feed | | |
| | Initial | Pre-Coat | | FA/kg | | Final |
| Run # | Weight (kg) | Total FA (kg) | FA + CWFI (kg) | Product (g) | Total FA (kg) | Product (kg) |
| 1 | 712 | 0.75 | 498 | 4.0 | 2.85 | 963 |
| 2a | 712 | 0.75 | 438 | 4.0 | 2.85 | Na |

TABLE 12-continued

Filter Aid Usage During Depth Filtration

| Run # | Initial Weight (kg) | Filter Aid Pre-Coat Total FA (kg) | Filter Aid Pre-Coat FA + CWFI (kg) | Filter Aid Body Feed FA/kg Product (g) | Total FA (kg) | Final Product (kg) |
|---|---|---|---|---|---|---|
| 2b | na | 0.75 | 440 | No additional FA added | | 850 | pH Adjustment: The pH adjustment step for the two lots is summarized in Table 13.

TABLE 13 pH Adjustment

| Run # | Initial Product pH | Initial Product Vol (kg) | NaOH Titrant Conc. | NaOH Titrant Vol. (kg) | Final Product pH | Final Product Vol (kg) |
|---|---|---|---|---|---|---|
| 1 | 4.93 | 963 | 0.4 N | 50.34 | 8.04 | 1016* |
| 2 | 4.90 | 850 | 0.4 N | 29.78 | 7.95 | 883* |

*The final weight does not exactly equal the sum of the initial product plus the titrant because the tank's load cells are rated at about 1% accuracy.

Membrane Filtration: The pH adjusted product from each lot was filtered through a single 30 inch 0.65 μm membrane filter. No signs of filter plugging were observed.

Procainamide Chromatography: The major steps of the procainamide chromatography are summarized in Table 14.

TABLE 14

Procainamide Chromatography

| Run # | CV (L) | Load FlowRate (ml/min) | Load Vol (kg) | Post Flush (EQ Buffer) FlowRate (ml/min) | Post Flush (EQ Buffer) Vol (CV) | Wash (EQ + 0.075 M NaCl) FlowRate (ml/min) | Wash (EQ + 0.075 M NaCl) Vol (CV) | [NaCl] (M) | Elution (EQ + NaCl) FlowRate (ml/min) | Elution (EQ + NaCl) Vol (kg) |
|---|---|---|---|---|---|---|---|---|---|---|
| 1 | 28 | 1100 | 1005 | 1100 | 4.8 | 155 | 51.5 | 0.5 | 800 | 87 |
| 2 | 28 | 1100 | 839 | 1100 | 4.4 | 155 | 80 | 1.0 | 800 | 53.2 |

Figure 6:
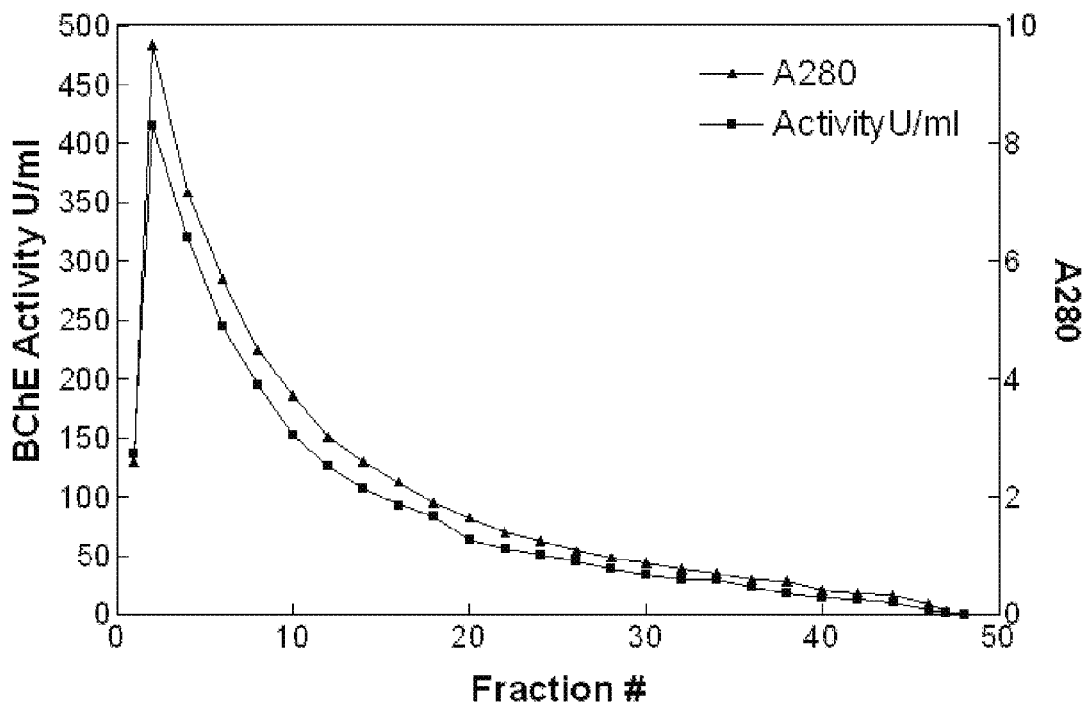
FIG. 6 is a graph of the procainamide affinity column Run #2 wherein activity and $A_{280}$ of each fraction are shown. A total of 37 fractions (#1 to #37), totaling about 53.2 kg of HuBChE were pooled.

The BChE activity in Run #1 continued to elute through the 2.0 M NaCl column regeneration step. It was determined that the sodium chloride concentration in the elution buffer was too low and was increased to 1.0 M for Run #2. As a result of the UV monitor being operated incorrectly in Run #2, the leading edge of the protein peak was missed and fraction collection was started late. Fortunately the "missed" BChE activity was collected with the void volume fraction. No material was lost, but the pooled volume was larger than expected. The elution fractions were assayed for BChE activity and total protein content. The results are presented graphically in FIG. 2 and FIG. 6.

Diafiltration: As a result of the procainamide column elution problems in Run #1, it was necessary to concentrate and diafilter the product in four separate steps. The product from Run #2 was processed in one step as planned. A summary of the concentration and diafiltration steps is presented in Table 15.

TABLE 15

Diafiltration Summary

| Run # | Initial Vol (kg) | Concentrated Vol (kg) | Diafiltered Volume (kg) |
|---|---|---|---|
| 1 (Fr 4-22) | 15.83 | 9.82 | 11.96 |
| 1 (Fr 23-33) | 8.8 | Not Recorded | Not Recorded |
| 1 (Fr 34) | 27.4 | 9.32 | 2 |
| 1 (Fr 35) | 20.6 | 6.65 | 4.3 |
| 2 | 10.72 | 12.0 | 12.4 |

DEAE Chromatography: The DEAE column in Run #1 was loaded in two steps as a result of the procainamide column elution problems. The major DEAE chromatography steps are summarized in Table 16.

TABLE 16

DEAE Chromatography

| Run # | CV (L) | Load FlowRate (ml/min) | Load Vol (kg) | Post Flush (EQ Buffer) FlowRate (ml/min) | Post Flush (EQ Buffer) Vol (CV) | Wash (EQ + 0.05 M NaCl) FlowRate (ml/min) | Wash (EQ + 0.05 M NaCl) Vol (CV) | Gradient Elution (EQ + NaCl) [NaCl] (M) | Gradient Elution (EQ + NaCl) FlowRate (ml/min) | Gradient Elution (EQ + NaCl) Vol (kg) |
|---|---|---|---|---|---|---|---|---|---|---|
| 1  | 18 | 75 | 11.96 | 75 | 3.2 | 75 | 4.9* | na | na | Na |
| 1b | 18 | 75 | 14.41 | 75 | 3   | 75 | 41   | 0.05-0.3 | 75 | 25.26 |
| 2  | 18 | 75 | 12.4  | 75 | 3.3 | 75 | 67   | 0.05-0.3 | 75 | 16.75 |

*Note: The EQ + 0.05 M NaCl wash was interrupted and the column was re-equilibrated with EQ buffer to allow the loading of additional product.

Figure 7:
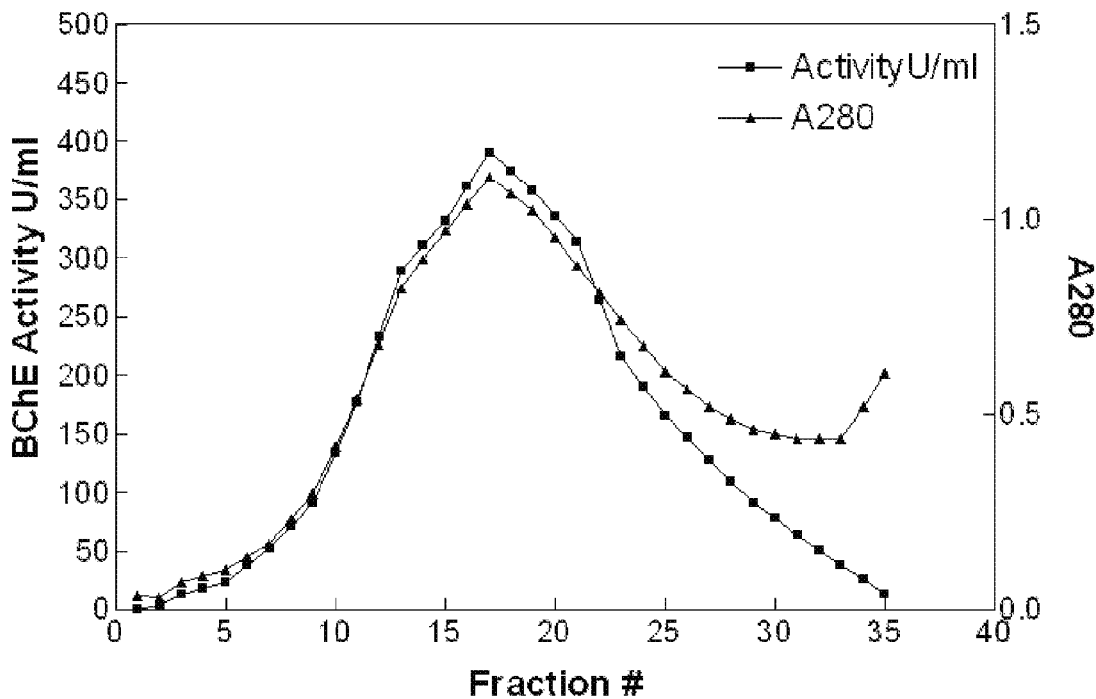
FIG. 7 is a graph of the DEAE column Run #2 wherein activity and $A_{280}$ Of each fraction are shown. A total of 16 fractions (#7 to #22), totaling 16.75 kg of HuBChE were pooled.

Both columns were eluted with a 10 CV gradient from EQ Buffer+0.05 M NaCl to EQ Buffer+0.3 M NaCl. Fractions were collected and assayed for BChE activity and total protein content. The results are presented graphically in FIG. 3 and FIG. 7. The activity eluted relatively early in the gradient suggesting that the gradient size and/or salt concentration could be reduced. The activity peak for Run #1 was pooled broader (25.25 kg) than the peak for Run #2 (16.75 kg). The peak in Run #2 was cut tighter on the trailing side and increased the purity of the final pooled product. The column was stripped with EQ Buffer+2.0 M NaCl solution and stored in 20% ethanol after each run.

Diafiltration: The DEAE pools were concentrated and diafiltered using a Millipore® Pellicon apparatus with 1.0 m² of 100 kD NMWCO membrane as summarized in Table 17.

TABLE 17

Diafiltration Summary

| Run # | DEAE Pool Vol. (kg) | Concentration Vol. (kg) | Diafiltration X Volumes | Diafiltration Final Vol (kg) |
|---|---|---|---|---|
| 1 | 25.26 | 5.15 | 5 | 8.35* |
| 2 | 16.75 | 4.75 | 5 | 7.80* |

*Final Volume includes two buffer flushes of Pellicon apparatus.

BChE and total protein recovery results: Quality Control laboratory test results for the two large-scale pre-clinical production runs are presented in Table 18.

TABLE 18

Recovery (Overall) of BChE and Total Protein in Pre-Clinical Runs

| Step | Large Scale Run #1 BChE Activity Units (×1000) | Large Scale Run #1 BChE Activity % | Large Scale Run #1 Total Protein Grams | Large Scale Run #1 Total Protein % | Large Scale Run #2 BChE Activity Units (×1000) | Large Scale Run #2 BChE Activity % | Large Scale Run #2 Total Protein Grams | Large Scale Run #2 Total Protein % |
|---|---|---|---|---|---|---|---|---|
| Resuspension | 9512 | 100 | 22500 | 100 | 10520 | 100 | 21390 | 100 |
| pH Adjustment to 4.9 | 9794 | 103.0 | 23780 | 105.9 | 10410 | 99.0 | 23420 | 109.5 |
| Centrifugation | 8295 | 87.2 | 19860 | 88.4 | 10470 | 99.6 | 19620 | 91.7 |
| Filter Aid Addition | 5985 | 62.9 | 13160 | 58.6 | 10020 | 95.3 | 18530 | 86.6 |
| Depth Filtration | 9341 | 98.2 | 15890 | 70.7 | 11380 | 108.2 | 12440 | 58.1 |
| pH Adjustment to 8.0 | 8433 | 88.7 | 16660 | 74.2 | 10130 | 96.3 | 12640 | 59.1 |
| 0.65 μm Filtration | 8744 | 91.9 | 17290 | 76.9 | 10040 | 95.5 | 12100 | 56.6 |
| Procainamide Column | 8478 | 89.1 | 62.2 | 0.28 | 6242 | 59.4 | 55.3 | 0.24 |
| DEAE Column | 5517 | 58.0 | 8.6 | 0.04 | 3543 | 33.7 | 8.7 | 0.04 |
| Concentration 1 | 5461 | 57.4 | 8.6 | 0.04 | 3810 | 36.2 | 5.2 | 0.02 |
| Concentration 2 | 5112 | 53.7 | 7.4 | 0.03 | 4355 | 41.4 | 6.2 | 0.03 |

CONCLUSIONS AND RECOMMENDATIONS

A major obstacle to the development of the purification method for HuBChE was the clarification of the resuspended Cohn Fraction IV-4 paste. The initial investigation was focused on developing a filtration method because the scale of the pre-clinical runs was too small to be handled efficiently by the Carr centrifuge. Unfortunately, depth filtration proved problematic with the available filtration equipment. After modifications to minimize wastage, the Carr centrifuge was used to clarify the resuspension. Future runs may be performed with a filter press using a relatively large filter area and a heavy filter aid body feed or other methods known in the art. Following centrifugation, depth filtration and membrane filtration were performed without difficulty. It was found that the 1.2 µm membrane could be eliminated and just the 0.65 µm membrane used for clarification.

The original procedure for the resuspension and procainamide chromatography steps is performed at pH 8.0. Prior to the DEAE step, the pH of the product is reduced to 4.5 to precipitate some additional protein. Starting with the second small scale run, the pH of the resuspension was reduced to 4.9 (this is the Cohn Fraction IV-5 method). Following centrifugation and depth filtration the pH is adjusted back to 8.0 (procainamide binding is more effective at pH 8.0). The product is then filtered through 1.2 µm and 0.65 µm membrane filters before loading onto the column. This method places both precipitation steps prior to the first column. The low pH treatment may also help reduce the lipid level in the product.

Following a long 67 CV wash with 0.05 M NaCl (in EQ Buffer), a 10 CV salt gradient from 0.05 M NaCl to 0.3 M NaCl was introduced for the elution of the DEAE column. This made a significant improvement in the purity of the final product. HuBChE was separated from large quantities of contaminating protein. This also suggests that it might also be possible to eliminate the lengthy 0.05 M NaCl wash by switching to a 0.0 to 0.3 M NaCl gradient. The theory being that the gradient would completely elute the low binding contaminants before eluting the HuBChE. Also, since the salt concentration of 0.3 M NaCl is higher than required to elute HuBChE, the concentration could probably be reduced to 0.2 M or 0.25 M NaCl resulting in a slight improvement in separation.

Batch chromatography was used in the original procedure. This may have been necessary as a result of inadequate clarification of the resuspension. With the improvements in clarification introduced in this study, the packed chromatography columns were run without any signs of excessive pressure or plugging. Column chromatography is more reproducible, easier to use, and will probably result in product of higher purity. It will also be easier to validate compared with batch methods.

In summary, a procedure has been developed which is adequate to produce large amounts of HuBChE preparations for pre-clinical uses. For clinical uses, viral inactivation steps such as solvent detergent and other methods known in the art may be performed. The DEAE wash may be reduced.

In summary, the present invention provides a method for the large-scale production of HuBChE. As used herein, "large-scale" refers to the use of starting materials, Cohn Fraction IV-4 paste in amounts greater than a few thousand grams, preferably more than about 2 kg to about 500 kg amounts, or about 2 to about 250 fold more than small-scale methods known in the art. The method of the present invention uses about a 1:10 dilution of Cohn Fraction IV-4 paste to water which is then adjusted to a pH of about 4.9 with sodium acetate rather than a 1:5 dilution of paste to sodium acetate buffer. The resuspension step of the present invention also differs from the prior art in that the solution is centrifuged in a continuous flow centrifuge at about 7663 rpm at a flow rate of about 4 kg/min. rather than 90 minutes at 13,700×g. Further, depth filtration is conducted with filters rather than dialysis. Specifically, according to the present invention, the suspension is adjusted to a pH of about 8.0 and then filtered with a 0.65 µm filter cartridge. Additionally, in the method of the present invention, affinity (procainamide column) and anion exchange (DEAE) chromatography were performed only once and procainamide affinity chromatography is performed first rather than DEAE anion exchange chromatography. The method of the present invention is superior to prior art methods as it results in recovery yields of about 60% having greater than about 99% purity and a specific activity of about 700 U/mg, whereas prior art methods result in yields of about 30% having about 80% purity (and up to about 90% purity using multiple washes and chromatography steps).

The HuBChE preparation made according to the present invention is safe, non-toxic, storage stable, highly bioavailable and proved to be an effective prophylactic treatment against OP agents. Thus, the HuBChE preparation of the present invention may be administered in an effective amount to a mammal such as a human. An "effective amount" is intended to mean an amount that is sufficient to treat, prevent or inhibit toxicity of an OP agent. The amount will vary depending upon factors such as the formulation and route of administration, but can nevertheless be routinely determined by one skilled in the art. An "effective amount" may be readily determined by one of ordinary skill by routine methods known in the art and refers to an amount that provides an observable desired change as compared with a control.

The skilled artisan will appreciate that certain factors may influence the dosage required to effectively treat a subject, including but not limited to the severity of toxicity and exposure, previous treatments, the general health and/or age of the subject, and other diseases present. Moreover, treatment of a subject can include a single treatment or a series of treatments. The effective dosage may increase or decrease over the course of a particular treatment. Changes in dosage may result and become apparent by standard diagnostic assays known in the art. Pharmaceutical formulations comprising the HuBChE preparation of the present invention may be prepared in a unit-dosage form appropriate for the desired mode of administration. The pharmaceutical formulations of the present invention may be administered by any suitable route including oral, rectal, nasal, topical (including buccal and sublingual), vaginal and parenteral (including subcutaneous, intramuscular, intravenous and intradermal). The pharmaceutical formulations may comprise an inert, pharmaceutically acceptable carrier or diluent. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like. The use of such media and agents for pharmaceutically active substances is well known in the art. Except insofar as any conventional media or agent is incompatible with HuBChE, use thereof in the formulation is contemplated.

Supplementary active compounds can also be incorporated into the formulations. Supplementary active compounds include antibiotics, antiprotozoal agents, antifungal agents, and antiproliferative agents known in the art, analgesics and other compounds commonly used to treat exposure to OP agents and biochemical warfare agents.

Antibiotics include penicillin, cloxacillin, dicloxacillin, methicillin, nafcillin, oxacillin, ampicillin, amoxicillin, bacampicillin, azlocillin, carbenicillin, mezlocillin, piperacillin, ticarcillin, azithromycin, clarithromycin, clindamycin, erythromycin, lincomycin, demeclocycline, doxycycline, minocycline, oxytetracycline, tetracycline, quinolone, cinoxacin, nalidixic acid, fluoroquinolone, ciprofloxacin, enoxacin, grepafloxacin, levofloxacin, lomefloxacin, norfloxacin, ofloxacin, sparfloxacin, trovafloxacin, bacitracin, colistin, polymyxin B, sulfonamide, trimethoprim-sulfamethoxazole, co-amoxyclav, cephalothin, cefuroxime, ceftriaxone, vancomycin, gentamicin, amikacin, metronidazole, chloramphenicol, nitrofurantoin, co-trimoxazole, rifampicin, isoniazid, pyrazinamide, kirromycin, thiostrepton, micrococcin, fusidic acid, thiolactomycin, fosmidomycin, and the like.

Antiprotozoal agents include chloroquine, doxycycline, mefloquine, metronidazole, eplornithine, furazolidone, hydroxychloroquine, iodoquinol, pentamidine, mebendazole, piperazine, halofantrine, primaquine, pyrimethamine sulfadoxine, doxycycline, clindamycin, quinine sulfate, quinidine gluconate, quinine dihydrochloride, hydroxychloroquine sulfate, proguanil, quinine, clindamycin, atovaquone, azithromycin, suramin, melarsoprol, eflornithine, nifurtimox, amphotericin B, sodium stibogluconate, pentamidine isethionate, trimethoprim-sulfamethoxazole, pyrimethamine, sulfadiazine, and the like.

Antifungal agents include amphotericin B, fluconazole, itraconazole, ketoconazole, potassium iodide, flucytosine, and the like.

Antiproliferative agents such as altretamine, amifostine, anastrozole, arsenic trioxide, bexarotene, bleomycin, busulfan, capecitabine, carboplatin, carmustine, celecoxib, chlorambucil, cisplatin, cisplatin-epinephrine gel, cladribine, cytarabine liposomal, daunorubicin liposomal, daunorubicin daunomycin, dexrazoxane, docetaxel, doxorubicin, doxorubicin liposomal, epirubicin, estramustine, etoposide phosphate, etoposide VP-16, exemestane, fludarabine, fluorouracil 5-FU, fulvestrant, gemicitabine, gemtuzumab-ozogamicin, goserelin acetate, hydroxyurea, idarubicin, ifosfamide, imatinib mesylate, irinotecan, letrozole, leucovorin, levamisole, liposomal daunorubicin, melphalan L-PAM, mesna, methotrexate, methoxsalen, mitomycin C, mitoxantrone, paclitaxel, pamidronate, pegademase, pentostain, porfimer sodium, streptozocin, talc, tamoxifen, temozolamide, teniposide VM-26, topotecan, toremifene, tretinoin, ATRA, valrubicin, vinorelbine, zoledronate, steroids, and the like.

Supplementary compounds also include antidotes known in the art such as botulism antitoxin, tetanus antitoxin, diphtheria antitoxin, and the like.

The formulations of the invention may be manufactured in manners generally known for preparing pharmaceutical and cosmetic compositions, e.g., using conventional techniques such as mixing, dissolving, granulating, dragee-making, levigating, emulsifying, encapsulating, entrapping or lyophilizing. The formulations may be formulated in a conventional manner using one or more physiologically acceptable carriers, which may be selected from excipients and auxiliaries that facilitate processing of the active compounds into preparations which can be used pharmaceutically or cosmetically.

In some embodiments, the HuBChE preparations are formulated with a carrier that will prolong the activity of the HuBChE such as a controlled release formulation, prevent or inhibit degradation or loss of activity, or prevent or inhibit loss of the HuBChE due to factors such as metabolism. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically or cosmetically acceptable carriers. These can be prepared according to methods known to those skilled in the art, for example, as described in U.S. Pat. No. 4,522,811.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A method for obtaining a human butyrylcholinesterase preparation from a Cohn Fraction IV-4 paste of human origin wherein said human butyrylcholinesterase preparation comprises 41.4 to 56.1% of the butyrylcholinesterase activity present in the Cohn Fraction IV-4 paste and has a purity of about 99% or more and a specific activity of about 700 U/mg, which comprises obtaining a Cohn Fraction IV-5 supernatant from the Cohn Fraction IV-4 paste;

subjecting the Cohn Fraction IV-5 supernatant to procainamide affinity chromatography only once by loading the human butyrylcholinesterase in the Cohn Fraction IV-5 supernatant onto an affinity chromatography column, washing the human butyrylcholinesterase on the affinity chromatography column with a volume of a wash solution that is 54 to 84 times the volume of chromatographic media used for procainamide affinity chromatography, and obtaining an eluent, subjecting the eluent to anion exchange chromatography only once, and obtaining the human butyrylcholinesterase preparation.

2. The method of claim 1, which further comprises adjusting the Cohn Fraction IV-5 supernatant to a pH of about 7.0 to about 9.0.

3. The method of claim 2, wherein the pH is about 8.0.

4. The method of claim 1, which further comprises filtering the Cohn Fraction IV-5 supernatant with a 0.65 μm filter cartridge.

5. The method of claim 1, wherein the anion exchange chromatography is conducted using a DEAE sepharose fast flow column.

6. A method for obtaining a human butyrylcholinesterase preparation from a Cohn Fraction IV-4 suspension, wherein said human butyrylcholinesterase preparation comprises 41.4 to 56.1% of the butyrylcholinesterase activity present in a Cohn Fraction IV-4 paste of human origin and has a purity of about 99% or more and a specific activity of about 700 U/mg, which consists essentially of
  obtaining a Cohn Fraction IV-5 supernatant from the Cohn Fraction IV-4 paste;
  subjecting the Cohn Fraction IV-5 supernatant to procainamide affinity chromatography only once by loading the human butyrylcholinesterase in the Cohn Fraction IV-5 supernatant onto an affinity chromatography column, washing the human butyrylcholinesterase on the affinity chromatography column with a volume of a wash solution that is 54 to 84 times the volume of chromatographic media used for procainamide affinity chromatography, and obtaining an eluent,
  subjecting the eluent to anion exchange chromatography only once, and
  obtaining the human butyrylcholinesterase preparation.

7. The method of claim 6, wherein the anion exchange chromatography is conducted using a DEAE sepharose fast flow column.

8. The method of claim 6, wherein the eluent is concentrated, diafiltered or both.

9. The method of claim 6, wherein the eluent is subjected to viral elimination.

10. The method of claim 6, wherein the human butyrylcholinesterase preparation is concentrated, diafiltered, filtered, or a combination thereof.

11. The method of claim 1, wherein the Cohn IV-5 supernatant is obtained by diluting the Cohn IV-4 paste by about nine-fold to about ten-fold in weight with water at a pH of about 4.9 to obtain a suspension and then centrifuging the suspension.

12. A method for obtaining a human butyrylcholinesterase preparation from a Cohn Fraction IV-4 paste of human origin which comprises obtaining a Cohn Fraction IV-5 supernatant from the Cohn Fraction IV-4 paste, subjecting the Cohn Fraction IV-5 supernatant to both an anion chromatography column and a procainamide affinity chromatography column to recover therefrom the human butyrylcholinesterase preparation, wherein the improvement comprises obtaining an eluent after washing the human butyrylcholinesterase on the procainamide affinity chromatography column with a volume of a wash solution that is 54 to 84 times the volume of chromatographic media in the procainamide affinity chromatography column, subjecting the eluent to the anion exchange chromatography column, and obtaining the human butyrylcholinesterase preparation.

13. The method of claim 12, wherein the Cohn Fraction IV-5 supernatant is subjected to procainamide affinity chromatography only once.

14. The method of claim 12, which further comprises adjusting the Cohn Fraction IV-5 supernatant to a pH of about 7.0 to about 9.0 or a pH of about 8.0.

15. The method of claim 12, wherein the wash solution comprises 25 mM sodium phosphate at pH 8.0, 1 mM EDTA, and either 0.05 M NaCl or 0.075 M NaCl.

* * * * *